United States Patent
Schmidt et al.

(10) Patent No.: US 12,312,387 B2
(45) Date of Patent: May 27, 2025

(54) COMPLEMENT INHIBITORS AND USES THEREOF

(71) Applicant: UNIVERSITAT ULM, Ulm (DE)

(72) Inventors: Christoph Schmidt, Westerheim (DE);
Hubert Schrezenmeier, Ulm (DE);
Markus Anliker, Amstetten (DE);
Britta Hoechsmann, Friedrichshafen (DE)

(73) Assignee: UNIVERSITAT ULM, Ulm (DE)

( * ) Notice: Subject to any disclaimer, the term of this patent is extended or adjusted under 35 U.S.C. 154(b) by 637 days.

(21) Appl. No.: 16/311,711

(22) PCT Filed: Jun. 28, 2017

(86) PCT No.: PCT/EP2017/065979
§ 371 (c)(1),
(2) Date: Dec. 20, 2018

(87) PCT Pub. No.: WO2018/002131
PCT Pub. Date: Jan. 4, 2018

(65) Prior Publication Data
US 2019/0202878 A1    Jul. 4, 2019

(30) Foreign Application Priority Data
Jun. 28, 2016 (EP) .................... 16176739

(51) Int. Cl.
*C07K 14/47* (2006.01)
*A61K 38/00* (2006.01)
*C07K 14/705* (2006.01)

(52) U.S. Cl.
CPC ............ *C07K 14/472* (2013.01); *A61K 38/00* (2013.01); *C07K 14/70596* (2013.01); *C07K 2319/01* (2013.01)

(58) Field of Classification Search
None
See application file for complete search history.

(56) References Cited

U.S. PATENT DOCUMENTS

| | | | |
|---|---|---|---|
| 9,540,626 B2 * | 1/2017 | Lambris | C07K 14/472 |
| 2008/0188404 A1 * | 8/2008 | Medof | C07K 14/70596 424/178.1 |

FOREIGN PATENT DOCUMENTS

| | | | |
|---|---|---|---|
| EP | 0 512 733 A2 | 11/1992 | |
| WO | 9508570 A1 | 3/1995 | |
| WO | 2005/069726 A2 | 8/2005 | |
| WO | 2010/034015 A2 | 3/2010 | |
| WO | 2013/142362 A1 | 9/2013 | |

OTHER PUBLICATIONS

Brodbeck, W. G. et al; "Structure/function studies of human decay accelerating factor." Immunol. (2000) 101 p. 104-111.*
Reynolds, Fred et al; "A functional proteomic method for biomarker discovery." PLoS ONE (2011) 6(7) e22471.*
Yampolsky, Lev Y and Stoltzfus, Arlin; "The exchangeability of amino acids in proteins." Genetics (2005) 170 p. 1459-1472.*
Ferreira, Viviana P. et al; "Complement control protein factor H: the good, the bad, and the inadequate." Mol. Immunol. (2010) 47(13) p. 2187-2197.*
Mammen, Mathai et al; "Polyvalent interactions in biological systems: implications for design and use of mulivalent ligands and inhibitors." Angew. Chem. Int. Ed. (1998) 37 p. 2754-2794.*
Da-Fei Feng and Russell F. Doolittle "Progressive Sequence Alignment as a Prerequisite to Correct Phylogenetic Trees", J. Mol. Evol., 1987, 25:351-360.
Higgins et al., "Fast and sensitive multiple sequence alignments on a microcomputer", Comp. Appl. Biosci., 1989, 5(2):151-3, Accession No. 2720464, abstract only.
Hillmen et al., "The Complement Inhibitor Eculizumab in Paroxysmal Nocturnal Hemoglobinuria", N. Engl. J. Med., 2006, 355:12. pp. 1233-1243.
Saul B. Needleman and Christian D. Wunsch "A General Method Applicable to the Search for Similarities in the Amino Acid Sequence of Two Proteins", J. Mol. Biol., 1970, 48, pp. 443-453.
Jacqueline Parkin and Bryony Cohen "An overview of the immune system", The Lancet, vol. 357, 2001, pp. 1777-1789.
Romay-Penabad et al., "Complement C5-inhibitor rEV576 (coversin) ameliorates in-vivo effects of antiphospholipid antibodies", Lupus, 2014, 13, pp. 1324-1326.
Ricklin et al., "Complement—a key system for immune surveillance and homeostasis", Nat. Immunol. 2010, 11(9):785-797.
Schmidt et al., "Translational Mini-Review Series on Complement Factor H: Structural and functional correlations for factor H", Clin. Exp. Immunol., 2008, 151: 14-24.
Schmidt et al., "Rational engineering of a minimized immune inhibitor with unique triple targeting properties", J. Immunol., 2013, 190(11); pp. 5712-5721.
Temple F. Smith "Comparison of Biosequences", Advances in Applied Mathematics 2, 1981, pp. 482-489.

(Continued)

*Primary Examiner* — Fred H Reynolds
(74) *Attorney, Agent, or Firm* — RAPHAEL BELLUM PLLC

(57) ABSTRACT

The present invention relates to a multi-domain polypeptide comprising (i) a first complement control protein repeat (CCP)-comprising domain being a convertase decay accelerating domain for convertases of the classical and alternative pathways of complement activation, (ii) a host cell recognition domain, and (iii) a second CCP-comprising domains with cofactor activity. The present invention further relates to a polynucleotide encoding said multi-domain polypeptide, to a vector comprising said polynucleotide, and to a host cell comprising said polynucleotide and/or said vector. Further, the present invention relates to the multi-domain polypeptide, the polypeptide, and the vector for use in medicine and for treating and/or preventing inappropriate complement activation and/or a disease having inappropriate complement activation as a symptom. Moreover, the present invention relates to methods and uses related to multi-domain polypeptide, the polypeptide, and the vector.

Figure 1:
Figure 1:
Figure 1:
Figure 1:
Figure 1:
Figure 1:

11 Claims, 6 Drawing Sheets
Specification includes a Sequence Listing.

(56) References Cited

OTHER PUBLICATIONS

P. Steinberger: "Synthetic construct encoding complement control domains of human CRI (CD35) that are implicated in complement split product binding", EMBL, May 16, 2011, Accession No. AEE81051, 1, XP055400263.
Harris et al, Generation of anti-complement "prodrugs": cleavable reagents for specific delivery of complement regulators to disease sites, The Journal of Biological Chemistry, vol. 278, No. 38, Issue of Sep. 19, pp. 36068-36076, 2003.

* cited by examiner

A

DAF(1-4)FH(19-20) long or short linker

DAF(1-4)FH(19-20)CR1(15-17)

sDAF

B

CR1(1-3)FH(19-20) long or short linker

CR1(1-3)FH(19-20)CR1(15-17)

CR1(1-3)    CR1(15-17)

A

B

A

B

C

A

B

COMPLEMENT INHIBITORS AND USES THEREOF

SEQUENCE LISTING

The Sequence Listing submitted herewith via EFS-Web is an ASCII text file (2018-12-20_Sequence_Listing.text, created on Dec. 19, 2018, 45748 bytes), and is incorporated by reference.

The present invention relates to a multi-domain polypeptide comprising (i) a first complement control protein repeat (CCP)-comprising domain being a convertase decay accelerating domain for convertases of the classical and alternative pathways of complement activation, (ii) a host cell recognition domain, and (iii) a second CCP-comprising domains with cofactor activity. The present invention further relates to a polynucleotide encoding said multi-domain polypeptide, to a vector comprising said polynucleotide, and to a host cell comprising said polynucleotide and/or said vector. Further, the present invention relates to the multi-domain polypeptide, the polypeptide, and the vector for use in medicine and for treating and/or preventing inappropriate complement activation and/or a disease having inappropriate complement activation as a symptom. Moreover, the present invention relates to methods and uses related to multi-domain polypeptide, the polypeptide, and the vector.

The immune system can be divided in two branches: the phylogenetically older innate immunity and the adaptive immune responses. An immune response by the adaptive, or acquired immune system, is typically more specific than an innate immune response. Other characteristics of the adaptive immune system are the development of an immunological memory and the typically observed delay between exposition of an antigen and the maximal immune response.

The innate immune system is highly conserved even in primitive organisms. The cellular effectors of this branch comprise mainly neutrophils, monocytes and macrophages, whereas the soluble innate immune effectors consist mainly of the complement system in addition to other effectors like acute phase proteins or pore-forming peptides (Parkin & Cohen (2001) The Lancet 357:1777-89.). The complement system consists of heat-labile components in serum, which were described by Paul Ehrlich to "complement" the antibody response against bacteria. Other functions of the complement system are opsonisation of microbial intruders, immune complexes, debris, apoptotic and necrotic cells to support their effective clearance through uptake by phagocytic cells (Ricklin et al. (2010) Nature Immunology 11:785-797). The complement system is organized in three activation pathways: the classical (CP), lectin (LP) and alternative pathway (AP).

Activation of the CP is typically achieved in an antibody-dependent manner via the complement component C1q, which acts as a pattern-recognition molecule (PRM). After a series of proteolytic activation events, the CP C3-convertase (C4bC2a) cleaves the complement component C3, which is central to all three complement activation pathways, to C3a, an anaphylatoxin and C3b (opsonin). Due to this cleavage, a conformational change occurs and a previously internal thioester bond reaches the protein surface of C3b. This active, and once it is exposed short lived, thioester bond can bind covalently to hydroxyl- and amino-groups of molecules localized on cell surfaces, or can be lysed ("quenched") by water. As a consequence opsonisation of cells with many C3b molecules can occur if the C3-convertase is not down regulated. The production of huge amounts of C3b molecules facilitates activation of C5 by C5 convertases. The C5-convertase cleaves C5 to C5a (the most potent anaphylatoxin) and C5b, which recruits the complement factors C6-9 to form the membrane attack complex (MAC) that assembles holes in cell membranes to lyse and kill.

The Lectin pathway (LP) is similarly organized as the CP. Activation occurs via recognition of pathogen-associated molecular patterns (PAMPs) or danger-associated molecular patterns (DAMPs). Within the LP, PAMPs or DAMPs can be detected by several pattern recognition molecules which are homologous to C1q (the pattern recognition molecule of the CP): mannose-binding lectin (MBL) and various types of collectins and ficolins. Subsequent to PAMP or DAMP, binding MBL undergoes conformational changes and then associates with MBL-associated serine proteases (MASPs). MBL is homologous in structure and function to C1q. In analogy to the CP, MASP2 proteolytically activates C2 into C2a and C2b, and C4 into C4a and C4b. The activated components can build the C3 convertase C4bC2a of the LP, which is identical to the CP and cleaves C3 into C3a and C3b. In analogy to the CP, in absence of strict regulation of the C3 convertase production of more C3b molecules fosters the activation of C5 via C5 convertases. Proteolytic activation of C5 is the starting point of the terminal and lytic complement pathway where C5b initiates formation of MAC.

The alternative pathway gets activated through a process of self-activation at low level. This process is called "tick-over" activation of C3. C3 molecules have an intrinsically metastable conformation. At all times, a small proportion of the C3 molecules undergo spontaneous conformational changes (activation) which exposes the previously internal thioester domain. The thioester can be quenched by water or attach indiscriminatingly (for self or foreign) to nucleophiles on a cell surface. Such "auto-activated" C3 is called C3 ($H_2O$) and is structurally similar to C3b molecules. C3b or C3 ($H_2O$) expose new protein surfaces that are hidden in C3. These new surfaces bind Factor B, another complement factor of the AP. When Factor B is bound to C3b or C3 ($H_2O$), it can be cleaved by the protease Factor D into Ba and Bb. Bb remains bound to C3 ($H_2O$) (or C3b) and constitutes the C3 convertase of the AP, C3bBb. In analogy to the CP and LP C3 convertases, C3bBb can produce C3b and C3a molecules by cleaving C3. The protein Properdin, a positive regulator of the AP, plays an important role by stabilizing the protein-protein interactions of the AP C3 convertase. If not regulated, any C3b generated by the alternative, classical or lectin pathway is able to build more C3 convertases of the AP and further amplify the number of produced C3b molecules in positive feedback loop. This step is called "amplification loop" of the AP. Thus, the three pathways of activation converge at the level of C3 activation and, if not regulated, cumulate in MAC formation.

Classical and lectin pathways are inactive until they get specifically activated through the sensing of pathogens or endogenous danger molecules. The AP, on contrary, is active all the time at a low level and indiscriminately produces C3b (or initially C3 ($H_2O$)) molecules. More than ten different regulatory proteins within the complement system are known. Some regulators inhibit right at the level of initiating the CP and LP, however the parts of the cascade that are most tightly controlled are the convertases, which act as amplifiers of the activation signal, and C3b, which builds the platform to form the C3-, and the inflammatory C5-convertases. There are also some regulators that specifically control the lytic MAC.

Regulatory proteins can be divided into decay accelerators which destabilize C3-convertase and lead to faster decay of the convertase. A further group involves proteins which degrade C3b or/and C4b, like Factor H and Factor I; to prevent non-specific degradation by the soluble protease Factor I, inactivation of C3b or C4b necessitates the presence of cofactor proteins that bind to the target and recruit Factor I (e.g. FH or CR1). A further group of regulators inhibits formation of MAC.

Many diseases, in particular hereditary diseases, are associated with a malfunction of complement, in particular overactivation of complement. Thus, in an effort to provide an artificial regulator of the complement system, a monoclonal antibody specifically binding to complement protein C5 and inhibiting terminal activation, eculizumab, was developed (Hillmen et al. (2006), NEJM355 (12): 1233). In a similar line of development, C5 inhibitory protein rEV576 (coversin) was developed (Romay-Penabad et al (2014), Lupus 23 (12): 1324). Further, a protein called "mini-FH", connecting complement control protein repeats (CCPs) 1-4 and 19-20 of complement factor H via a linker was obtained (WO 2013/142362 A1); however, the latter only inhibits the alternative pathway.

There is, thus, a need in the art for improved complement inhibitors avoiding the drawbacks of the prior art. This problem is solved by the means and methods disclosed herein.

Accordingly, the present invention relates to a multi-domain polypeptide comprising
(i) a first complement control protein repeat (CCP)-comprising domain being a convertase decay accelerating domain for convertases of the classical and alternative pathways of complement activation,
(ii) a host cell recognition domain, and
(iii) a second CCP-comprising domain.

Also, the present invention relates to a multi-domain polypeptide comprising
(i) a first complement control protein repeat (CCP)-comprising domain comprising an amino acid sequence at least 70% identical to CCPs 1 to 3 of a complement receptor type 1 (CR1) and/or comprising an amino acid sequence at least 70% identical to CCPs 1 to 4 of a decay accelerating factor (DAF),
(ii) a host cell recognition domain comprising an amino acid sequence at least 70% identical to CCPs 6 to 8 or to CCPs 19 to 20 of a complement Factor H, and
(iii) a second CCP-comprising domain, comprising an amino acid sequence at least 70% identical to CCPs 8 to 10 and/or to CCPs 15 to 17 of a CR1.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention. Moreover, if not otherwise indicated, the term "about" relates to the indicated value with the commonly accepted technical precision in the relevant field, preferably relates to the indicated value±20%, more preferably ±10%, most preferably ±5%.

The term "complement control protein repeat", which is also referred to as "CCP", "short complement-like repeat", "short consensus repeat" or "SCR" in the art is, in principle, known in the art and was reviewed, e.g. in Schmidt et al. (2008), Clin Exp Immunol. 151 (1): 14-24). CCPs are peptide sequences comprising approx. 60 to 70 amino acids including four conserved cysteine residues forming two disulfide bonds and a conserved tryptophan, with considerable sequence variation of the residual amino acids. Besides binding to complement proteins C3b and/or C4b, CCPs were found to mediate further activities, including decay accelerating activity and Factor I cofactor activity as specified herein below.

The term "first CCP-comprising domain", as used herein, relates to a domain of the multi-domain polypeptide as specified herein being a convertase decay accelerating domain for convertases of the classical and alternative pathways of complement activation. Thus, preferably, the first CCP-comprising domain comprises at least one CCP having decay accelerating activity on C3 convertases of both the alternative and the classical pathway of complement activation. The term "decay accelerating activity" as used herein, relates to the property of a CCP or CCP-comprising domain to mediate decay, preferably inactivation, of the C3 convertase of the alternative pathway of complement activation, i.e. C3bBb, and/or of the C3 convertase of the classical pathway of complement activation, i.e. C4bC2a. Preferably, decay accelerating activity of a CCP is determined by surface plasmon resonance (SPR) as specified herein in the Examples. Preferably, the first CCP-comprising domain comprises of from two to ten, preferably of from two to five, more preferably of from three to four CCPs having or contributing to the aforesaid activity. Preferably, the first CCP-comprising domain comprises CCPs 1 to 3 of a complement receptor type 1 (CR1), preferably of human CR1, as specified herein below; and/or comprises CCPs 1 to 4 of a decay accelerating factor (DAF), preferably human DAF, as specified herein below. Preferably, the first CCP-comprising domain comprises CCPs 1 to 3 of a complement receptor type 1 (CR1), as in the naturally occurring sequence; and/or comprises CCPs 1 to 4 of a decay accelerating factor (DAF), as in the naturally occurring sequence.

Preferably, the first CCP-comprising domain comprises, preferably consists of, an amino acid sequence as shown in SEQ ID NO: 1 or an amino acid sequence being at least 70%, preferably at least 80%, more preferably at least 90%, most preferably at least 95% identical to SEQ ID NO: 1 and having the activity of being a convertase decay accelerating domain for convertases of the classical and alternative pathways of complement activation. More preferably, the first CCP-comprising domain comprises, preferably consists of, an amino acid sequence as shown in SEQ ID NO:1. Also preferably, the first CCP-comprising domain comprises, preferably consists of, an amino acid sequence as shown in SEQ ID NO:2 or an amino acid sequence being at least 70%, preferably at least 80%, more preferably at least 90%, most preferably at least 95% identical to SEQ ID NO:2 and having the activity of being a convertase decay accelerating domain for convertases of the classical and alternative pathways of complement activation. More preferably, the first CCP-comprising domain comprises, preferably consists of, an amino acid sequence as shown in SEQ ID NO:2.

Preferably, the first CCP-comprising domain comprises at least one, preferably at least two, more preferably at least three CCPs having binding activity for complement factors C3b and/or C4b. As will be understood by the skilled person, one or more CCPs having binding activity for complement factors C3b and/or C4b may be CCPs different from the CCP or CCPs having decay accelerating activity as specified above; preferably, the CCP(s) having binding activity for complement factors C3b and/or C4b are the CCP(s) having decay accelerating activity as specified above. The term "binding activity for complement factors C3b and/or C4b" is understood by the skilled person. Preferably, the term relates to the property of the first CCP-comprising domain and/or of at least one of its CCPs to bind to at least one of complement proteins C3b and C4b with measurable affinity. Preferably, binding affinity of a CCP or a CCP-comprising domain to C3b or C4b is determined by surface plasmon resonance (SPR) as specified herein in the Examples.

The term "complement receptor type 1" or "CR1" is, in principle, known to the skilled person as relating to a member of the regulators of complement activation (RCA) family of proteins which is also known as C3b/C4b receptor or cluster of differentiation 35 protein (CD35). Preferably, CR1 is a mammalian CR1, more preferably, CR1 is human CR1. Most preferably, CR1 is human CR1 having an amino acid sequence as specified in Genbank Acc. No. P17927.3 GI: 290457678.

The term "decay accelerating factor" or "DAF" is, in principle, also known to the skilled person as relating to a cell surface-bound regulator of the complement system which is also known as cluster of differentiation 55 protein (CD55). Preferably, DAF is a mammalian DAF, more preferably human DAF. Most preferably, DAF is human DAF having an amino acid sequence as specified in Genbank Acc. No. P08174.4 GI: 60416353.

The term "second CCP-comprising domain", as used herein, relates to a domain of the multi-domain polypeptide comprising at least one CCP. Preferably, said second CCP-comprising domain is not directly contiguous with said first CCP-comprising domain, i.e. said second CCP-comprising domain is not connected to said first CCP-comprising domain by a contiguous series of peptide bonds or, preferably, said first and second CCP-comprising domains are separated by a domain having binding activity neither to C3b nor to C4b. Thus, preferably, in case the multi-domain polypeptide is a fusion polypeptide, the first and second CCP-comprising domains preferably are separated by at least a host cell recognition domain. Preferably, the second CCP-comprising domain comprises of from two to ten, preferably of from two to five, more preferably of from three to four CCPs, preferably having or contributing to the activity as described below. Preferably, the second CCP-comprising domain comprises CCPs 8 to 10 and/or 15 to 17 of a CR1, preferably of human CR1 as specified herein above. More preferably, the second CCP-comprising domain comprises CCPs 15 to 17 of CR1, preferably of human CR1. Even more preferably, the second CCP-comprising domain comprises, preferably consists of, an amino acid sequence as shown in SEQ ID NO:3 or an amino acid sequence being at least 70%, preferably at least 80%, more preferably at least 90%, most preferably at least 95% identical to SEQ ID NO:3, preferably having Factor I cofactor activity as described herein below. Most preferably, the second CCP-comprising domain comprises, preferably consists of, an amino acid sequence as shown in SEQ ID NO:3.

Preferably, the second CCP-comprising domain comprises at least one, preferably at least two, more preferably at least three, most preferably of from three to four CCPs having binding activity for complement factors C3b and/or C4b, preferably further having Factor I cofactor activity. The term "Factor I cofactor activity", as used herein, relates to the property of a compound, preferably a CCP or a CCP-comprising domain, of binding to C3b and/or C4b and mediating proteolytic degradation of said C3b and/or C4b by Factor I. Preferably, Factor I cofactor activity is determined as indicated herein in the Examples.

The term "host cell recognition domain", as used herein, relates to a domain of the multi-domain polypeptide having the activity of binding to host cell surface markers, preferably polyanionic carbohydrates comprising sialic acids and/or glycosaminoglycans, and/or having the activity of binding to complement factor C3b degradation products, preferably to iC3b and/or C3dg or C3d. Preferably, the host cell recognition domain comprises at least one, preferably at least two CCPs having binding activity to host cell surface markers, preferably polyanionic carbohydrates comprising sialic acids and/or glycosaminoglycans and/or having binding activity to complement factor C3b degradation products, preferably to iC3b and/or C3dg or C3d. Preferably, the host cell recognition domain comprises CCPs 6 to 8 and/or 19 to 20 of a complement Factor H, preferably a human complement Factor H as specified herein above. More preferably, the host cell recognition domain comprises, preferably consists of, an amino acid sequence as shown in SEQ ID NO:4 or an amino acid sequence being at least 70%, preferably at least 80%, more preferably at least 90%, most preferably at least 95% identical to SEQ ID NO:4, preferably having binding activity to host cell surface markers, preferably polyanionic carbohydrates comprising sialic acids and/or glycosaminoglycans and/or having binding activity to complement factor C3b degradation products, preferably to iC3b and/or C3dg. More preferably, the host cell recognition domain comprises, preferably consists of, an amino acid sequence as shown in SEQ ID NO:4. Preferably, binding activity to host cell surface markers and binding activity to complement factor C3b degradation products of a CCP or of a host cell recognition domain is determined by surface plasmon resonance (SPR) as specified herein in the Examples.

As used in this specification, the term "multi-domain polypeptide" relates to any chemical molecule comprising at least the polypeptide domains as specified herein below. It is to be understood that the chemical linkage between the domains need not necessarily be a peptide bond. It is also envisaged by the present invention that the chemical bond between the domains is an ester bond, a disulfide bond, or any other suitable covalent chemical bond known to the skilled artisan. Also envisaged are non-covalent bonds with a dissociation constant so low that a domain will only dissociate to a negligible extent from the other domains. Preferably, the dissociation constant for said non-covalent bond is less than $10^{-5}$ mol/l (as it is the case with the Strep-Tag: Strep-Tactin binding), less than $10^{-6}$ mol/l (as it is the case in the Strep-TagII: Strep-Tactin binding), less than $10^{-8}$ mol/l, less than $10^{-10}$ mol/l, or less than $10^{-12}$ mol/l (as it is the case for the Streptavidin: Biotin binding). Methods of determining dissociation constants are well known to the skilled artisan and include, e.g., spectroscopic titration methods, surface plasmon resonance measurements, equilibrium dialysis and the like. Moreover, it is also envisaged that the binding between the domains of the multi-domain polypeptide is indirect, e.g. that the domains comprise a tag with affinity for biotin and are bound to a further molecule or particle comprising biotin moieties. Preferably, the chemical linkage between the domains is a peptide bond, i.e., preferably, the multi-domain polypeptide is a fusion polypeptide comprising or consisting of the domains of the present invention. Preferably, at least two domains of the multi-domain polypeptide are connected by a linker peptide. Suitable linker peptides are, in principle, known in the art. Preferred linker peptides comprise or, preferably, consist of glycine and/or proline residues. More preferably, a linker peptide is a poly-glycine linker peptide. Most preferably, a linker peptide, in particular a linker peptide linking a first CCP-comprising domain and a host cell recognition domain as specified elsewhere herein, is a linker comprising, preferably consisting of, 14 or 15 glycine residues. In a preferred embodiment, the polypeptide consists of the components as described herein.

Preferably, reference to polypeptides, in particular multi-domain polypeptides, and/or domains, in particular CCP-comprising domains, includes variants of the specific polypeptides and domains described herein. As used herein, the terms "polypeptide variant" and "domain variant" relates to any chemical molecule comprising at least the domain or domains as specified herein, but differing in structure from said polypeptide or domain indicated. Preferably, a polypeptide variant or a domain variant comprises a peptide having an amino acid sequence corresponding to an amino acid sequence of from 25 to 500, more preferably of from 30 to 300, most preferably, of from 35 to 150 consecutive amino acids comprised in a polypeptide or domain as specified herein. Moreover, it is to be understood that a polypeptide variant or domain variant as referred to in accordance with the present invention shall have an amino acid sequence which differs due to at least one amino acid substitution, deletion and/or addition, wherein the amino acid sequence of the variant is still, preferably, at least 50%, 60%, 70%, 80%, 85%, 90%, 92%, 95%, 97%, 98%, or 99% identical with the amino acid sequence of the specific polypeptide or domain. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the sequence it is compared to for optimal alignment. The percentage is calculated by determining, preferably over the full length of the peptide, the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Polypeptide variants or domain variants referred to above may be derived from allelic variants or any other species specific homologs, paralogs, or orthologs. Moreover, polypeptide variants referred to herein include fragments of the specific polypeptides or the aforementioned types of variants as long as these fragments and/or variants comprise the domains as referred to above. Such fragments may be or be derived from, e.g., degradation products or splice variants of the polypeptides. Further included are variants which differ due to posttranslational modifications such as phosphorylation, glycosylation, ubiquitinylation, sumoylation, or myristylation, by including non-natural amino acids, and/or by being peptidomimetics.

As used herein, the term "domain comprising an amino acid sequence at least 70% identical to X" relates to a domain comprising a variant of X as specified above having an amino acid sequence at least 70% identical to X. Preferably, the domain comprising an amino acid sequence at least 70% identical to X is a variant of X having the activity of X, more preferably as specified herein.

Thus, preferably, the multi-domain polypeptide of the present invention and variants thereof have the activity of being an inhibitor of complement activation, i.e. have the activity of inhibiting the complement reaction, preferably in vitro and/or in vivo. Preferably, the multi-domain polypeptide and its variants have the activity of inhibiting at least two, more preferably all three activation pathways of the complement system. More preferably, the multi-domain polypeptide and variants thereof have the activity of inhibiting at least the alternative pathway and the classical pathway of complement activation, preferably have the activity of inhibiting at least the alternative pathway, the classical pathway, and the lectin pathway of complement activation.

Preferably, the multi-domain polypeptide comprises at least two of its domains, preferably comprises all three of its domains as a contiguous polypeptide sequence, i.e., the multi-domain polypeptide preferably is a fusion polypeptide comprising said three domains. Preferably, in principle, the three domains may be comprised in such a fusion polypeptide in any order deemed appropriate by the skilled person. More preferably, the multi-domain polypeptide comprises said domains in the order N-terminus, first CCP-comprising domain, host cell recognition domain, second CCP-comprising domain, C-terminus. Even more preferably, the multi-domain polypeptide comprises, preferably consists of an amino acid sequence as shown in SEQ ID NO: 5 or 6 or is a variant thereof as specified herein above, wherein, preferably, said variant still has the activity of being an inhibitor of complement activation as specified above.

Advantageously, it was found in the work underlying the present invention that the compounds described herein have complement-inhibiting activity and are, particularly suited for inhibiting all three known pathways of complement activation. Surprisingly, the dissociation constant of the compounds of the present invention for factor C3b was found to be in the 20 nM to 40 nM range. Moreover, the compounds were found to prevent hemolysis induced via the alternative pathway at a concentration of approximately 75 nM to 150 nM and hemolysis induced via the classical pathway at a concentration of less than 100 nM.

The definitions made above apply mutatis mutandis to the following. Additional definitions and explanations made further below also apply for all embodiments described in this specification mutatis mutandis.

The present invention further relates to a polynucleotide encoding the multi-domain polypeptide of the present invention.

The term "polynucleotide", as used in accordance with the present invention relates to a polynucleotide comprising a nucleic acid sequence which encodes a multi-domain polypeptide comprising the domains as specified herein above. A polynucleotide encoding a multi-domain polypeptide comprising the aforementioned domains has been obtained in accordance with the present invention by synthesizing a polynucleotide encoding the relevant domains using well known techniques.

Thus, the polynucleotide, preferably, comprises the nucleic acid sequence shown in SEQ ID NO: 7 or 13, encoding a polypeptide having an amino acid sequence as shown in SEQ ID NO: 5, and/or comprises the nucleic acid sequence shown in SEQ ID NO:8 or 14, encoding a polypeptide having an amino acid sequence as shown in SEQ ID NO:6. It is to be understood that a polypeptide having an amino acid sequence as shown in SEQ ID NOs: 5 or 6 may be also encoded due to the degenerated genetic code by other polynucleotides as well.

Moreover, the term "polynucleotide", as used in accordance with the present invention, further encompasses variants of the aforementioned specific polynucleotides. The polynucleotide variants, preferably, comprise a nucleic acid sequence characterized in that the sequence can be derived from the aforementioned specific nucleic acid sequences shown in SEQ ID NO: 7, 8, 13, or 14 by at least one nucleotide substitution, addition and/or deletion whereby the variant nucleic acid sequence shall still encode a polypeptide comprising the activities as specified above. Variants include polynucleotides comprising nucleic acid sequences which are at least 70%, at least 75%, at least 80%, at least 85%, at least 90%, at least 95%, at least 98% or at least 99% identical to the nucleic acid sequences shown in SEQ ID NO: 7, 8, 13, or 14. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences shown in SEQ ID NO: 5 or 6. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution, 25, 351-360, 1987, Higgins et al., CABIOS, 5 1989:151-153) or the programs Gap and BestFit (Needleman and Wunsch (J. Mol. Biol. 48; 443-453 (1970)) and Smith and Waterman (Adv. Appl. Math. 2; 482-489 (1981))), which are part of the GCG software packet (Genetics Computer Group, 575 Science Drive, Madison, Wisconsin, USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6' sodium chloride/sodium citrate (=SSC) at approximately 45° C., followed by one or more wash steps in 0.2' SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5' SSC (pH 7.2). If organic solvent is present in the abovementioned buffer, for example 50% formamide, the temperature under standard conditions is approximately 42° C. The hybridization conditions for DNA: DNA hybrids are preferably for example 0.1' SSC and 20° C. to 45° C., preferably between 30° C. and 45° C. The hybridization conditions for DNA: RNA hybrids are preferably, for example, 0.1'SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequence of the polynucleotide or the amino acid sequence of the polypeptide of the present invention with sequences of other CCPs. As a template, DNA or cDNA from animals, preferably mammals, more preferably humans, may be used.

A polynucleotide comprising a fragment of any of the aforementioned nucleic acid sequences is also encompassed as a polynucleotide of the present invention. The fragment shall encode a polypeptide comprising the domains specified above and which, preferably, still has the activity as specified above. Accordingly, the polypeptide may comprise or consist of the domains of the present invention conferring the said biological activities. A fragment as meant herein, preferably, comprises at least 50, at least 100, at least 250 or at least 500 consecutive nucleotides of the aforementioned nucleic acid sequence or encodes an amino acid sequence comprising at least 20, at least 30, at least 50, at least 80, at least 100 or at least 150 consecutive amino acids of the aforementioned amino acid sequence.

The polynucleotides of the present invention either consist of the aforementioned nucleic acid sequences or comprise the aforementioned nucleic acid sequences. Thus, they may contain further nucleic acid sequences as well. Specifically, the polynucleotides of the present invention may encode fusion proteins wherein one partner of the fusion protein is a multi-domain polypeptide being encoded by a nucleic acid sequence recited above. Such fusion proteins may comprise as additional part other polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

The polynucleotide of the present invention shall be provided, preferably, either as an isolated polynucleotide (i.e. isolated from its natural context) or in genetically modified form. The polynucleotide, preferably, is DNA, including cDNA, or is RNA. The term encompasses single as well as double stranded polynucleotides. Moreover, comprised are also chemically modified polynucleotides including naturally occurring modified polynucleotides such as glycosylated or methylated polynucleotides or artificial modified one such as biotinylated polynucleotides.

Thus, preferably, the polynucleotide of the present invention a) is a polynucleotide having at least 70% sequence identity to SEQ ID NO: 7, 8, 13, or 14, b) encodes a polypeptide having at least 70% sequence identity to SEQ ID NO: 5 or 6, and/or c) is a polynucleotide capable of hybridizing under stringent conditions stringent conditions to SEQ ID NO: 7, 8, 13, or 14. More preferably, the polynucleotide a) is a polynucleotide comprising, preferably consisting of the nucleic acid sequence of SEQ ID NO: 7, 8, 13, or 14, and/or b) encodes a polypeptide comprising, preferably consisting of the amino acid sequence of SEQ ID NO: 5 or 6. Preferably, the polynucleotide of the present invention encodes a multi-domain polypeptide having an activity as specified above.

The present invention further relates to a vector comprising the polynucleotide of the present invention.

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells.

More preferably, in the vector of the invention the polynucleotide is operatively linked to expression control sequences allowing expression in prokaryotic and/or eukaryotic cells or isolated fractions thereof. Expression of said polynucleotide comprises transcription of the polynucleotide, preferably into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (InVitrogene) or pSPORT1 (GIBCO BRL). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Preferably, the vector is a vector mediating expression of the polynucleotide of the present invention in a host cell. The skilled artisan knows how to select combinations of vectors and host cells for propagation of a vector and/or for expression of a protein encoded by the vector.

Furthermore, the present invention relates to a host cell comprising the polynucleotide or the vector of the present invention.

A "host cell", as used herein, relates to a bacterial, archaeal, or eukaryotic cell with the capacity to propagate the vector of the present invention and/or to produce a multi-domain polypeptide encoded on the vector or the polynucleotide of the invention. Preferably, the host cell is a bacterial cell from the species *Escherichia coli*, a lepidopteran, a mouse, rat, or a human cell; more preferably, the cell is a yeast cell, preferably of the genus *Pichia*, more preferably a *Pichia pastoris* cell. Preferably, the host cell is a cell cultivated in vitro. In a further preferred embodiment, the host cell is a cell in vivo, preferably a retinal pigment epithelial cell, an endothelial cell within the choroid vasculature, and/or another cell within the retina or the choroidea.

The present invention also relates to a multi-domain polypeptide according to the present invention, a polynucleotide according to the present invention, or a vector according to the present invention for use in medicine. Moreover, the present invention also relates to a multi-domain polypeptide according to the present invention, a polynucleotide according to the present invention, or a vector according to the present invention for treating and/or preventing inappropriate complement activation and/or a disease having inappropriate complement activation as a symptom.

As used herein, the term "inappropriate complement activation" relates to a complement activation which is, in timing and/or amplitude, exceeding the normal level of complement activation under the given circumstances. Thus, preferably, inappropriate complement activation is complement activation exceeding, preferably significantly exceeding, the extent of complement activation of a healthy reference, preferably an apparently healthy subject, under the given circumstances. Preferably, inappropriate complement activation is complement activation causing symptoms of disease in a patient. Symptoms of inappropriate complement activation are known in the art and include hemolysis, macular degeneration, episodic swellings, e.g. in hereditary angioedema, and the like. Preferably, inappropriate complement activation is determined by determining complement factor C3 and/or C4 activity in a sample.

As is known to the skilled person, a variety of diseases is associated and/or caused by inappropriate complement activation. Thus, preferably, the present invention also relates to a multi-domain polypeptide according to the present invention, a polynucleotide according to the present invention, or a vector according to the present invention for treating and/or preventing a disease having inappropriate complement activation as a symptom. Preferably, said disease having inappropriate complement activation as a symptom is selected from the list consisting of ischemia reperfusion injury, antibody-mediated graft rejection, posttransplantation thrombotic microangiopathy, autoimmune hemolytic anemia, acute and delayed hemolytic transfusion reaction, cold agglutinine disease, rheumatoid arthritis, aquaporin-4-antibody-positive neuromyelitis optica, CD59-deficiency, C3-Glomerulopathy, atypical hemolytic uremic syndrome, paroxysmal nocturnal hemoglobinuria, and age-related macular degeneration.

The term "treating", as used herein, refers to ameliorating the diseases or disorders referred to herein or the symptoms accompanied therewith, preferably to a significant extent. Said treating as used herein also includes an entire restoration of health with respect to the diseases or disorders referred to herein. It is to be understood that treating as used in accordance with the present invention may not be effective in all subjects to be treated. However, the term shall preferably require that a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population.

The term "preventing", as used herein, refers to retaining health with respect to the diseases or disorders referred to herein for a certain period of time in a subject. It will be understood that the said period of time is dependent on the amount of the drug compound which has been administered and individual factors of the subject discussed elsewhere in this specification. It is to be also understood that prevention may not be effective in all subjects treated with the compound according to the present invention. However, the term preferably requires that a statistically significant portion of subjects of a cohort or population are effectively prevented from suffering from a disease or disorder referred to herein or its accompanying symptoms. Preferably, a cohort or population of subjects is envisaged in this context which normally, i.e. without preventive measures according to the present invention, would develop a disease or disorder as referred to herein. Whether a portion is statistically significant can be determined without further ado by the person skilled in the art using various well known statistic evaluation tools discussed elsewhere in this specification.

The present invention also relates to a multi-domain polypeptide according to the present invention, a polynucleotide according to the present invention, or a vector according to the present invention for treating and/or preventing inappropriate complement activation and/or a disease having inappropriate complement activation as a symptom in combination with a complement protein C5 inhibiting polypeptide, preferably Eculizumab.

The present invention further relates to a complement protein C5 inhibiting polypeptide, preferably Eculizumab, or rEV576 (coversin) for treating and/or preventing inappropriate complement activation and/or a disease having inappropriate complement activation as a symptom in combination with a multi-domain polypeptide according to the present invention, a polynucleotide according to the present invention, or a vector according to the present invention.

The term "complement protein C5" is understood by the skilled person as relating to the protein which is cleaved to yield complement proteins C5a and C5b after activation of the complement pathway. Correspondingly, a "complement protein C5 inhibiting polypeptide" is a polypeptide, preferably an antibody, more preferably a monoclonal antibody, specifically recognizing and inhibiting the complement protein C5. Preferably, the complement protein C5 inhibiting polypeptide is an antibody specifically binding to C5 and inhibiting terminal activation; more preferably, the complement protein C5 inhibiting polypeptide is Eculizumab (CAS NO: 219685-50-4). Also preferably, complement protein C5 inhibiting polypeptide is rEV576 (coversin).

The present invention further relates to a combined preparation for simultaneous, separate or sequential use comprising (i) a multi-domain polypeptide according to the present invention and (ii) a complement protein C5 inhibiting polypeptide, preferably Eculizumab, or rEV576 (coversin).

The term "combined preparation", as referred to in this application, relates to a preparation comprising the pharmaceutically active compounds of the present invention in one preparation. Preferably, the combined preparation is comprised in a container, i.e. preferably, said container comprises all pharmaceutically active compounds of the present invention. Preferably, said container comprises the pharmaceutically active compounds of the present invention as separate formulations, i.e. preferably, one formulation of the multi-domain polypeptide and one formulation of the complement protein C5 inhibiting polypeptide. As will be understood by the skilled person, the term "formulation" relates to a, preferably pharmaceutically acceptable, mixture of compounds, comprising or consisting of at least one pharmaceutically active compound of the present invention. Preferably, the combined preparation comprises a complement protein C5 inhibiting polypeptide and a multi-domain polypeptide in a single solid pharmaceutical form, e.g. a tablet, wherein, more preferably, one compound of the present invention is comprised in an immediate or fast release formulation, and the second compound of the present invention is comprised in a slow or retarded release formulation; more preferably, the compounds of the present invention are comprised in two separate, preferably liquid, formulations; said separate liquid formulations, preferably are for injection, preferably at different parts of the body of a subject.

Preferably, the combined preparation is for separate or for combined administration. "Separate administration", as used herein, relates to an administration wherein at least two of the pharmaceutically active compounds of the present invention are administered via different routes and/or at different parts of the body of a subject. E.g. one compound may be administered by enteral administration (e.g. orally), whereas a second compound is administered by parenteral administration (e.g. intravenously). Preferably, the combined preparation for separate administration comprises at least two physically separated preparations for separate administration, wherein each preparation contains at least one pharmaceutically active compound; said alternative is preferred e.g. in cases where the pharmaceutically active compounds of the combined preparation have to be administered by different routes, e.g. parenterally and orally, due to their chemical or physiological properties. Conversely, "combined administration" relates to an administration wherein the pharmaceutically active compounds of the present invention are administered via the same route, e.g. orally or, preferably, intravenously.

Also preferably, the combined preparation is for simultaneous or for sequential administration. "Simultaneous administration", as used herein, relates to an administration wherein the pharmaceutically active compounds of the present invention are administered at the same time, i.e., preferably, administration of the pharmaceutically active compounds starts within a time interval of less than 15 minutes, more preferably, within a time interval of less than 5 minutes. Most preferably, administration of the pharmaceutically active compounds starts at the same time, e.g. by swallowing a tablet comprising the pharmaceutically active compounds, or by swallowing a tablet comprising one of the pharmaceutically active compounds and simultaneous injection of the second compound, or by applying an intravenous injection of a solution comprising one pharmaceutically active compound and injecting second compound in different part of the body. Conversely, "sequential administration, as used herein, relates to an administration causing plasma concentrations of the pharmaceutically active compounds in a subject enabling the synergistic effect of the present invention, but which, preferably, is not a simultaneous administration as specified herein above. Preferably, sequential administration is an administration wherein administration of the pharmaceutically active compounds, preferably all pharmaceutically active compounds, starts within a time interval of 1 or 2 days, more preferably within a time interval of 12 hours, still more preferably within a time interval of 4 hours, even more preferably within a time interval of one hour, most preferably within a time interval of 5 minutes.

Preferably, the combined preparation is a pharmaceutically compatible combined preparation. The terms "pharmaceutically compatible preparation" and "pharmaceutical composition", as used herein, relate to compositions comprising the compounds of the present invention and optionally one or more pharmaceutically acceptable carrier. The compounds of the present invention can be formulated as pharmaceutically acceptable salts. Preferred acceptable salts are acetate, methylester, HCl, sulfate, chloride and the like. The pharmaceutical compositions are, preferably, administered topically or, more preferably, systemically. Suitable routes of administration conventionally used for drug administration are oral, intravenous, subcutaneous, or parenteral administration as well as inhalation. However, depending on the nature and mode of action of a compound, the pharmaceutical compositions may be administered by other routes as well. Moreover, the compounds can be administered in combination with other drugs either in a common pharmaceutical composition or as separated pharmaceutical compositions as specified elsewhere herein, wherein said separated pharmaceutical compositions may be provided in form of a kit of parts. Preferably, the combined preparation is an extended release preparation with regard to one or more of the compounds.

The compounds are, preferably, administered in conventional dosage forms prepared by combining the drugs with standard pharmaceutical carriers according to conventional procedures. These procedures may involve mixing, granulating and compressing or dissolving the ingredients as appropriate for the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, a solid, a gel or a liquid. Exemplary of solid carriers are lactose, terra alba, sucrose, talc, gelatin, agar, pectin, acacia, magnesium stearate, stearic acid, and the like. Exemplary liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pennsylvania.

The diluent(s) is/are selected so as not to affect the biological activity of the compound or compounds. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers, reactive oxygen scavengers, and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of from 1 to 1500 mg; however, doses below or above this exemplary range are envisioned, especially considering the aforementioned factors. Generally, the regimen as a regular administration of the pharmaceutical composition should be in the range of 100 μg to 100 mg units per day. If the regimen is a continuous infusion, it should also be in the range of 100 μg to 100 mg units per kilogram of body weight per minute, respectively. Preferably, extended release preparations of each drug are injected from once per 1 week to once per 2 months or even at longer intervals. Progress can be monitored by periodic assessment. Preferred doses and concentrations of the compounds of the present invention are specified elsewhere herein.

By means of example, a plasma concentration of the multi-domain polypeptide preferably is not less than 25 nM, more preferably not less than 50 nM. Also preferably, a plasma concentration of the multi-domain polypeptide is in the range of from 20 nM to 20 μM, more preferably of from 50 nM to 5 μM. Effective concentrations of a complement protein C5 inhibiting polypeptide, in particular Eculizumab, are known in the art. Due to the synergistic effect of the multi-domain polypeptides of the present invention, the effective concentrations for a complement protein C5 inhibiting polypeptide in combined treatment may be lower.

The pharmaceutical compositions and formulations referred to herein are, preferably, administered at least once, e.g. in case of extended release formulations, in order to treat or ameliorate or prevent a disease or condition recited in this specification. However, the said pharmaceutical compositions may be administered more than one time, for example from one to four times daily up to a non-limited number of days. Also some compounds with a short clearance time may be applied as infusion in blood stream to provide effective dose in whole body during long treatment time.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

The present invention also relates to a medicament comprising (i) a multi-domain polypeptide, (ii) a complement protein C5 inhibiting polypeptide, and (iii) at least one pharmaceutically acceptable carrier; and to said medicament for use in treatment and/or prevention as specified above.

The term "medicament" is understood by the skilled person. As will be understood, the definitions given herein above for the term "combined preparation", preferably, apply to the term medicament of the present invention mutatis mutandis.

Further, the present invention relates to a method for treating and/or preventing inappropriate complement activation and/or a disease having inappropriate complement activation as a symptom in a subject comprising administering an effective dose of a multi-domain polypeptide according to the present invention, a polynucleotide according to the present invention, or a vector according to the present invention to said subject, thereby treating and/or preventing inappropriate complement activation and/or a disease having inappropriate complement activation as a symptom in said subject.

The method for treating and/or preventing of the present invention, preferably, is an in vivo method. Moreover, it may comprise steps in addition to those explicitly mentioned above. For example, further steps may relate, e.g., to diagnosing inappropriate complement activation and/or a disease having inappropriate complement activation as a symptom, or administering additional compounds, e.g. a complement protein C5 inhibiting polypeptide. Moreover, one or more of said steps may be performed by automated equipment.

The term "subject", as used herein, relates to an animal having a complement system, preferably to a mammal. More preferably, the subject is cattle, a pig, sheep, horse, cat, dog, mouse, or rat, most preferably a human.

Moreover, the present invention relates to an in vitro method for preventing or reducing the degree of complement activation comprising applying a multi-domain polypeptide according to the present invention, a polynucleotide according to the present invention, or a vector according to the present invention to a reaction mixture comprising complement factors, thereby preventing or reducing the degree of complement activation in said reaction mixture.

The in vitro method for preventing or reducing the degree of complement activation of the present invention may comprise steps in addition to those explicitly mentioned above. For example, further steps may relate, e.g., to introducing the polynucleotide or the vector of the present invention into a host cell, or determining the degree of complement activation in said reaction mixture. Moreover, one or more of said steps may be performed by automated equipment.

Further, the present invention relates to a use of a multi-domain polypeptide according to the present invention, a polynucleotide according to the present invention, or a vector according to the present invention for treating and/or preventing inappropriate complement activation and/or a disease having inappropriate complement activation as a symptom; and to a use of a multi-domain polypeptide according to the present invention, a polynucleotide according to the present invention, or a vector according to the present invention for manufacturing a medicament for treating and/or preventing inappropriate complement activation and/or a disease having inappropriate complement activation as a symptom.

In view of the above, the following embodiments are preferred:

1. A multi-domain polypeptide comprising
   (i) a first complement control protein repeat (CCP) being a convertase decay accelerating domain for convertases of the classical and alternative pathways of complement activation,
   (ii) a host cell recognition domain, and
   (iii) a second CCP-comprising domain.
2. A multi-domain polypeptide comprising
   (i) a first complement control protein repeat (CCP) domain comprising an amino acid sequence at least 70% identical to CCPs 1 to 3 of a complement receptor type 1 (CR1) and/or comprising an amino acid sequence at least 70% identical to CCPs 1 to 4 of a decay accelerating factor (DAF), (ii) a host cell recognition domain comprising an amino acid sequence at least 70% identical to CCPs 6 to 8 or to CCPs 19 to 20 of a complement Factor H, and (iii) a second CCP-comprising domain, comprising an amino acid sequence at least 70% identical to CCPs 8 to 10 and/or to CCPs 15 to 17 of a CR1.

3. The multi-domain polypeptide of embodiment 1 or 2, wherein said first and/second CCP-comprising domain comprises a multitude of CCPs.

4. The multi-domain polypeptide of any one of embodiments 1 to 3, wherein said first and/or second CCP-comprising domain comprises of from two to ten, preferably of from two to five, more preferably of from three to four CCPs.

5. The multi-domain polypeptide of any one of embodiments 1 to 4, wherein said first CCP-comprising domain comprises CCPs 1 to 3 of a complement receptor type 1 (CR1), preferably of human CR1; and/or comprises CCPs 1 to 4 of a decay accelerating factor (DAF), preferably human DAF.

6. The multi-domain polypeptide of any one of embodiments 1 to 5, wherein said first CCP-comprising domain comprises, preferably consists of, an amino acid sequence as shown in SEQ ID NO: 1 or an amino acid sequence being at least 70% identical to SEQ ID NO:1.

7. The multi-domain polypeptide of any one of embodiments 1 to 6, wherein said first CCP-comprising domain comprises, preferably consists of, an amino acid sequence as shown in SEQ ID NO:1.

8. The multi-domain polypeptide of any one of embodiments 1 to 7, wherein said first CCP-comprising domain comprises, preferably consists of, an amino acid sequence as shown in SEQ ID NO:2 or an amino acid sequence being at least 70% identical to SEQ ID NO:2.

9. The multi-domain polypeptide of any one of embodiments 1 to 8, wherein said first CCP-comprising domain comprises, preferably consists of, an amino acid sequence as shown in SEQ ID NO:2.

10. The multi-domain polypeptide of any one of embodiments 1 to 9, wherein said second CCP-comprising domain comprises CCPs 8 to 10 and/or 15 to 17 of CR1, preferably of human CR1.

11. The multi-domain polypeptide of any one of embodiments 1 to 10, wherein said second CCP-comprising domain comprises CCPs 15 to 17 of CR1, preferably of human CR1.

12. The multi-domain polypeptide of any one of embodiments 1 to 11, wherein said second CCP-comprising domain comprises, preferably consists of, an amino acid sequence as shown in SEQ ID NO:3 or an amino acid sequence being at least 70% identical to SEQ ID NO: 3.

13. The multi-domain polypeptide of any one of embodiments 1 to 12, wherein said second CCP-comprising domain comprises, preferably consists of, an amino acid sequence as shown in SEQ ID NO:3.

14. The multi-domain polypeptide of any one of embodiments 1 to 13, wherein said host cell recognition domain comprises CCPs 6 to 8 and/or 19 to 20 of a complement Factor H, preferably a human complement Factor H.

15. The multi-domain polypeptide of any one of embodiments 1 to 14, wherein said host cell recognition domain comprises, preferably consists of, an amino acid sequence as shown in SEQ ID NO:4 or an amino acid sequence being at least 70% identical to SEQ ID NO:4.

16. The multi-domain polypeptide of any one of embodiments 1 to 15, wherein said host cell recognition domain comprises, preferably consists of, an amino acid sequence as shown in SEQ ID NO:4.

17. The multi-domain polypeptide of any one of embodiments 1 to 16, wherein said multi-domain polypeptide comprises at least two of said domains, preferably comprises all three of said domains as a contiguous polypeptide sequence.

18. The multi-domain polypeptide of any one of embodiments 1 to 17, wherein said multi-domain polypeptide comprises said domains in the order N-terminus, first CCP-comprising domain, host cell recognition domain, second CCP-comprising domain, C-terminus.

19. The multi-domain polypeptide of any one of embodiments 1 to 18, wherein at least two of said domains are connected by a linker peptide, preferably a poly-glycine linker peptide.

20. The multi-domain polypeptide of any one of embodiments 1 to 19, wherein said first CCP-comprising domain and said host cell recognition domain are connected by a linker comprising, preferably consisting of, 14 or 15 glycine residues.

21. The multi-domain polypeptide of any one of embodiments 1 to 20, wherein said multi-domain polypeptide comprises, preferably consists of an amino acid sequence as shown in SEQ ID NO: 5 or 6 or an amino acid sequence being at least 70% identical to SEQ ID NO:5 or 6.

22. The multi-domain polypeptide of any one of embodiments 1 to 21, wherein said multi-domain polypeptide comprises, preferably consists of an amino acid sequence as shown in SEQ ID NO: 5 or 6.

23. The multi-domain polypeptide of any one of embodiments 1 to 22, wherein said first CCP-comprising domain comprises at least one, preferably at least two, more preferably at least three CCPs having binding activity for complement factors C3b and C4b.

24. The multi-domain polypeptide of any one of embodiments 1 to 23, wherein said second CCP-comprising domain comprises at least one, preferably at least two, more preferably at least three CCPs having binding activity for complement factors C3b and/or C4b, preferably further having Factor I cofactor activity.

25. The multi-domain polypeptide of any one of embodiments 1 to 24, wherein said host cell recognition domain comprises at least one, preferably at least two CCPs having binding activity to complement factor C3b degradation products, preferably to iC3b and/or C3dg and/or C3d; and/or having binding activity to host cell surface markers, preferably polyanionic carbohydrates comprising sialic acids and/or glycosaminoglycans.

26 The multi-domain polypeptide of any one of embodiments 1 to 25, wherein said multi-domain polypeptide has the activity of inhibiting the complement reaction.

27. The multi-domain polypeptide of any one of embodiments 1 to 26, wherein said multi-domain polypeptide has the activity of inhibiting at least two, preferably, more preferably all three activation pathways of the complement system.

28. The multi-domain polypeptide of any one of embodiments 1 to 27, wherein said multi-domain polypeptide has the activity of inhibiting at least the alternative pathway and the classical pathway of complement activation, preferably has the activity of inhibiting at least the alternative pathway, the classical pathway, and the lectin pathway of complement activation.
29. A polynucleotide encoding a multi-domain polypeptide of any one of embodiments 1 to 28.
30. The polynucleotide of embodiment 29, wherein said polynucleotide
a) is a polynucleotide having at least 70% sequence identity to SEQ ID NO: 7, 8, 13, or 14,
b) encodes a polypeptide having at least 70% sequence identity to SEQ ID NO: 5 or 6, and/or
c) is a polynucleotide capable of hybridizing under stringent conditions stringent conditions to SEQ ID NO: 7, 8, 13, or 14.
31. The polynucleotide of embodiment 29 or 30, wherein said polynucleotide
a) is a polynucleotide comprising, preferably consisting of the nucleic acid sequence of SEQ ID NO: 7, 8, 13, or 14, and/or
b) encodes a polypeptide comprising, preferably consisting of the amino acid sequence of SEQ ID NO: 5 or 6.
32. A vector comprising the polynucleotide of any one of embodiments 29 to 31.
33. A host cell comprising the polynucleotide of any one of embodiments 29 to 31 and/or the vector of embodiment 32.
34. A multi-domain polypeptide according to any one of embodiments 1 to 28, a polynucleotide according to any one of embodiments 29 to 31, or a vector according to embodiment 33 for use in medicine.
35. A multi-domain polypeptide according to any one of embodiments 1 to 28, a polynucleotide according to any one of embodiments 29 to 31, or a vector according to embodiment 33 for treating and/or preventing inappropriate complement activation and/or a disease having inappropriate complement activation as a symptom.
36. A multi-domain polypeptide according to any one of embodiments 1 to 28, a polynucleotide according to any one of embodiments 29 to 31, or a vector according to embodiment 33 for treating and/or preventing ischemia reperfusion injury, antibody-mediated graft rejection, posttransplantation thrombotic microangiopathy, autoimmune hemolytic anemia, acute and delayed hemolytic transfusion reaction, cold agglutinin disease, rheumatoid arthritis, aquaporin-4-antibody-positive neuromyelitis optica, CD59-deficiency, C3-Glomerulopathy, atypical or typical hemolytic uremic syndrome, paroxysmal nocturnal hemoglobinuria, and/or age-related macular degeneration.
37. A multi-domain polypeptide according to any one of embodiments 1 to 28, a polynucleotide according to any one of embodiments 29 to 31, or a vector according to embodiment 33 for treating and/or preventing inappropriate complement activation and/or a disease having inappropriate complement activation as a symptom in combination with a complement protein C5 inhibiting polypeptide, preferably Eculizumab or rEV576 (coversin).
38. A complement protein C5 inhibiting polypeptide, preferably Eculizumab for treating and/or preventing inappropriate complement activation and/or a disease having inappropriate complement activation as a symptom in combination with a multi-domain polypeptide according to any one of embodiments 1 to 28, a polynucleotide according to any one of embodiments 29 to 31, or a vector according to embodiment 33.
39. A combined preparation for simultaneous, separate or sequential use comprising (i) a multi-domain polypeptide according to any one of embodiments 1 to 28 and (ii) a complement protein C5 inhibiting polypeptide, preferably Eculizumab or rEV576 (coversin).
40. A method for treating and/or preventing inappropriate complement activation and/or a disease having inappropriate complement activation as a symptom in a subject comprising administering an effective dose of a multi-domain polypeptide according to any one of embodiments 1 to 28, a polynucleotide according to any one of embodiments 29 to 31, or a vector according to embodiment 33 to said subject, thereby treating and/or preventing inappropriate complement activation and/or a disease having inappropriate complement activation as a symptom in said subject.
41. An in vitro method for preventing or reducing the degree of complement activation comprising applying a multi-domain polypeptide according to any one of embodiments 1 to 28 to a reaction mixture comprising complement factors, thereby preventing or reducing the degree of complement activation in said reaction mixture.
42. Use of a multi-domain polypeptide according to any one of embodiments 1 to 28, a polynucleotide according to any one of embodiments 29 to 31, or a vector according to embodiment 33 for treating and/or preventing inappropriate complement activation and/or a disease having inappropriate complement activation as a symptom.
43. Use of a multi-domain polypeptide according to any one of embodiments 1 to 28, a polynucleotide according to any one of embodiments 29 to 31, or a vector according to embodiment 33 for manufacturing a medicament for treating and/or preventing inappropriate complement activation and/or a disease having inappropriate complement activation as a symptom.

All references cited in this specification are herewith incorporated by reference with respect to their entire disclosure content and the disclosure content specifically mentioned in this specification.

FIGURE LEGENDS

FIG. 1: Schematic representation of the constructs used.

Figure 2:
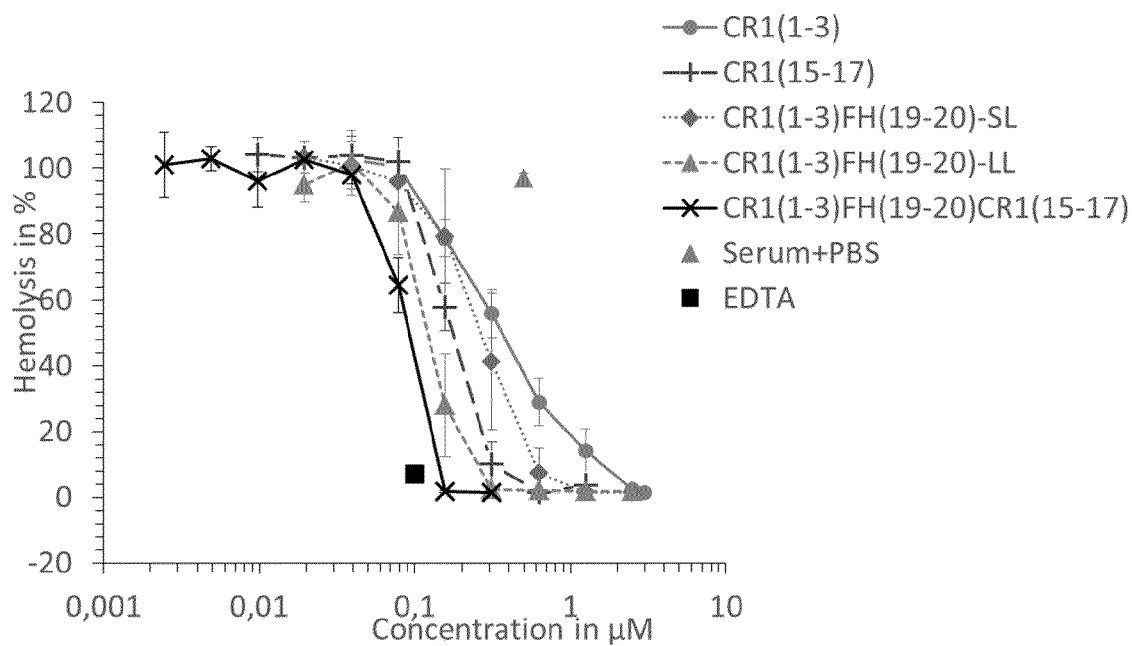
Figure 2:
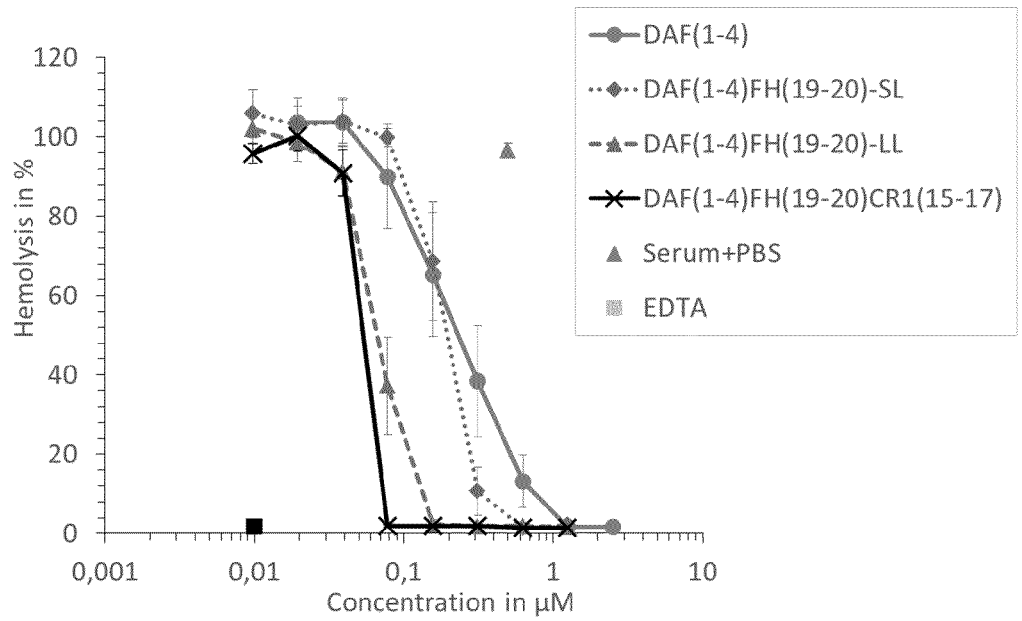

FIG. 2: Inhibition of alternative pathway mediated hemolysis by CR1-(A) and DAF-(B) derived constructs. x-axis: concentration of inhibitor (construct), y-axis: hemolysis in %.

Figure 3:
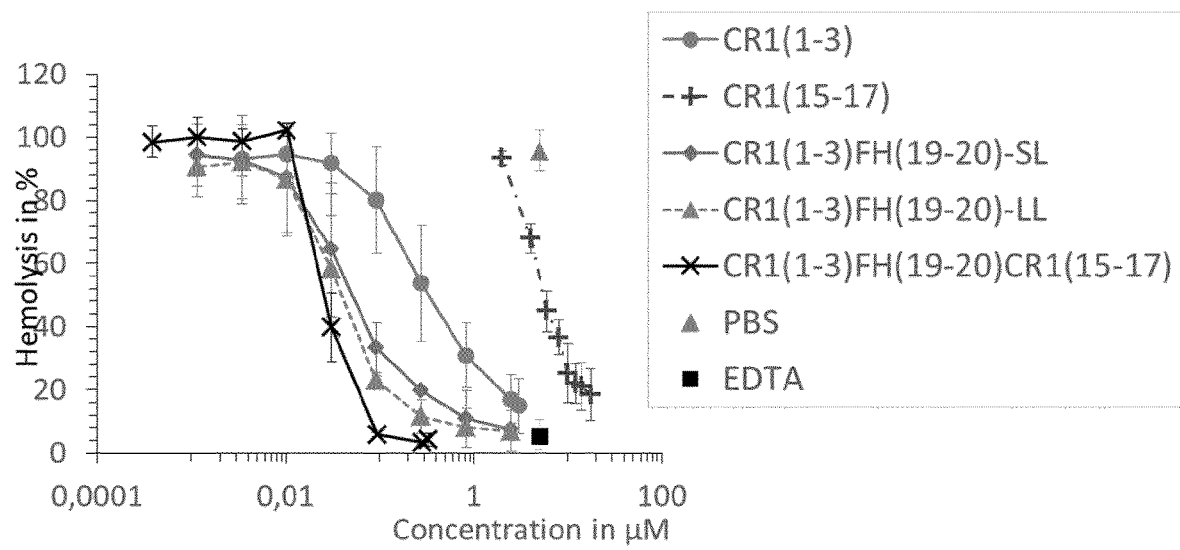
Figure 3:
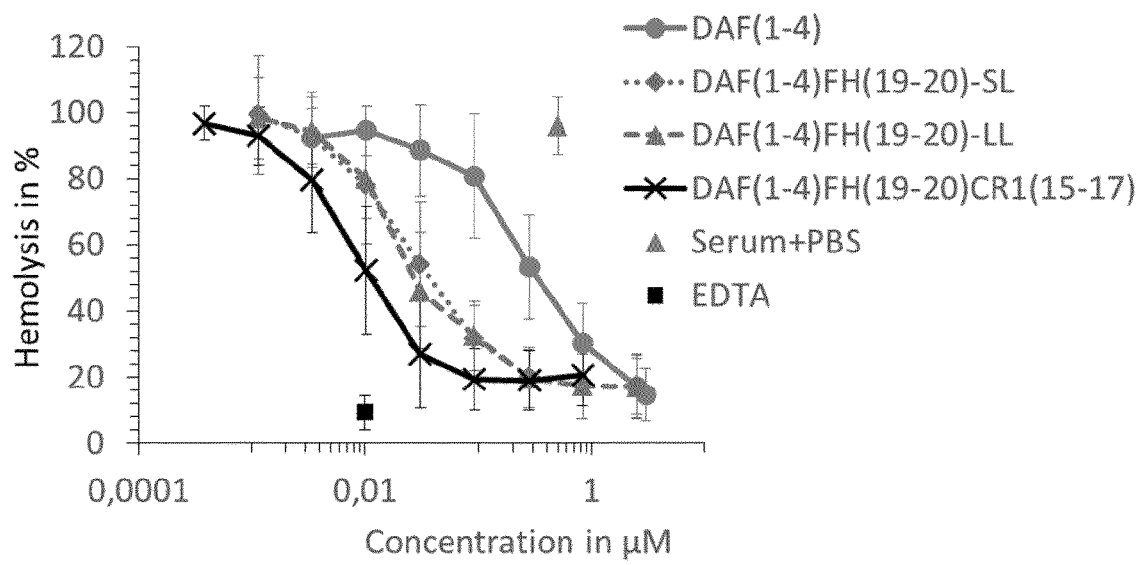
Figure 3:
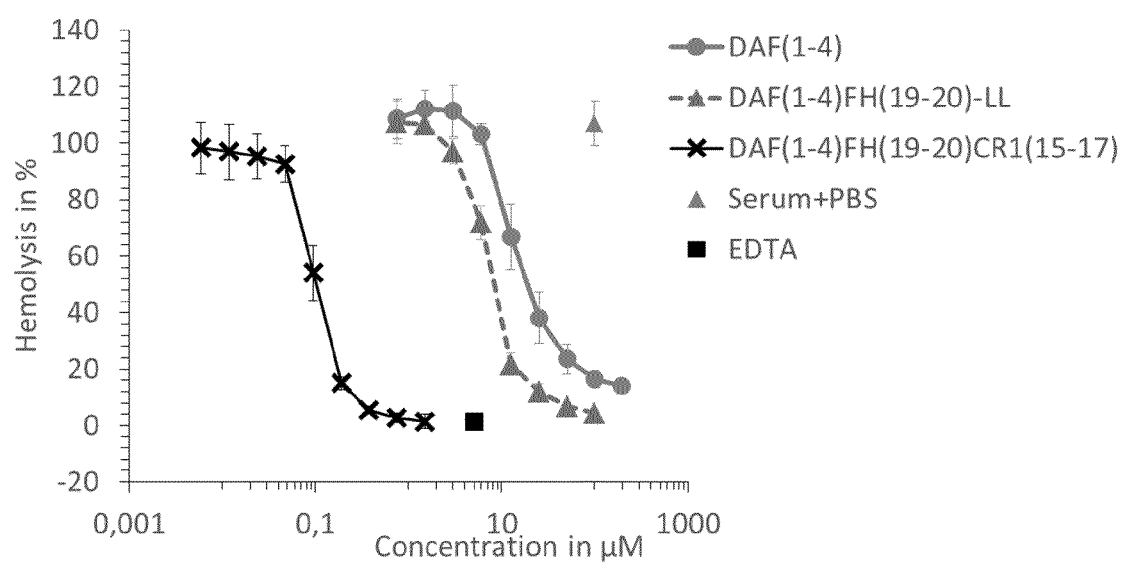

FIG. 3: Inhibition of classical pathway mediated hemolysis by CR1 (A) and DAF (B)-derived constructs in 5% serum. (C) as in (B), but in 75% serum. x-axis: concentration of inhibitor (construct), y-axis: hemolysis in %.

Figure 4:
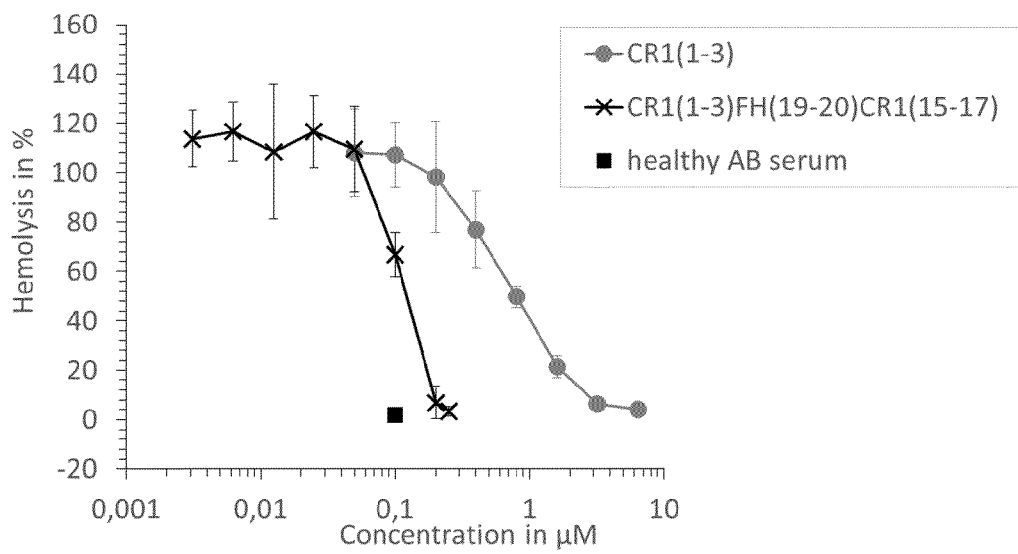
Figure 4:
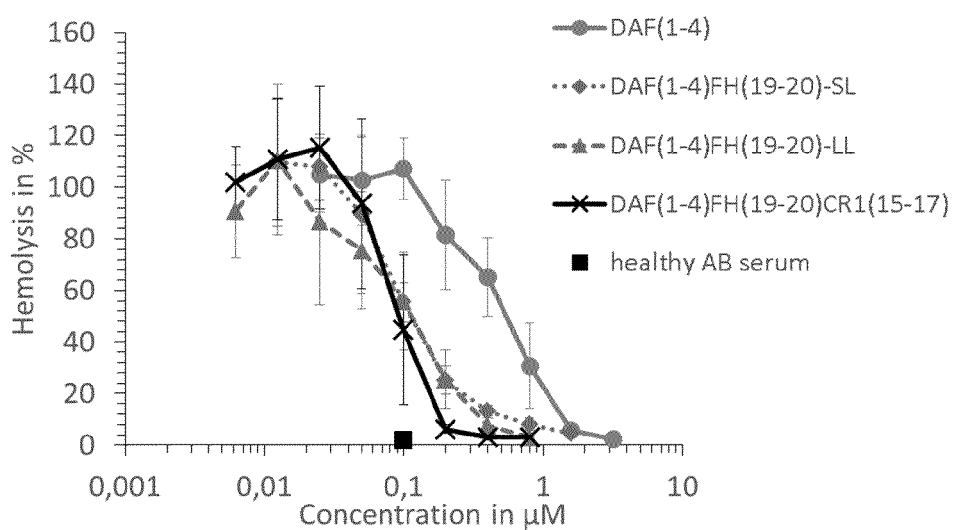

FIG. 4: Inhibition of alternative pathway mediated hemolysis of PNH-RBCs by CR1 (A) and DAF (B)-derived constructs. x-axis: concentration of inhibitor (construct), y-axis: hemolysis in %.

Figure 5:
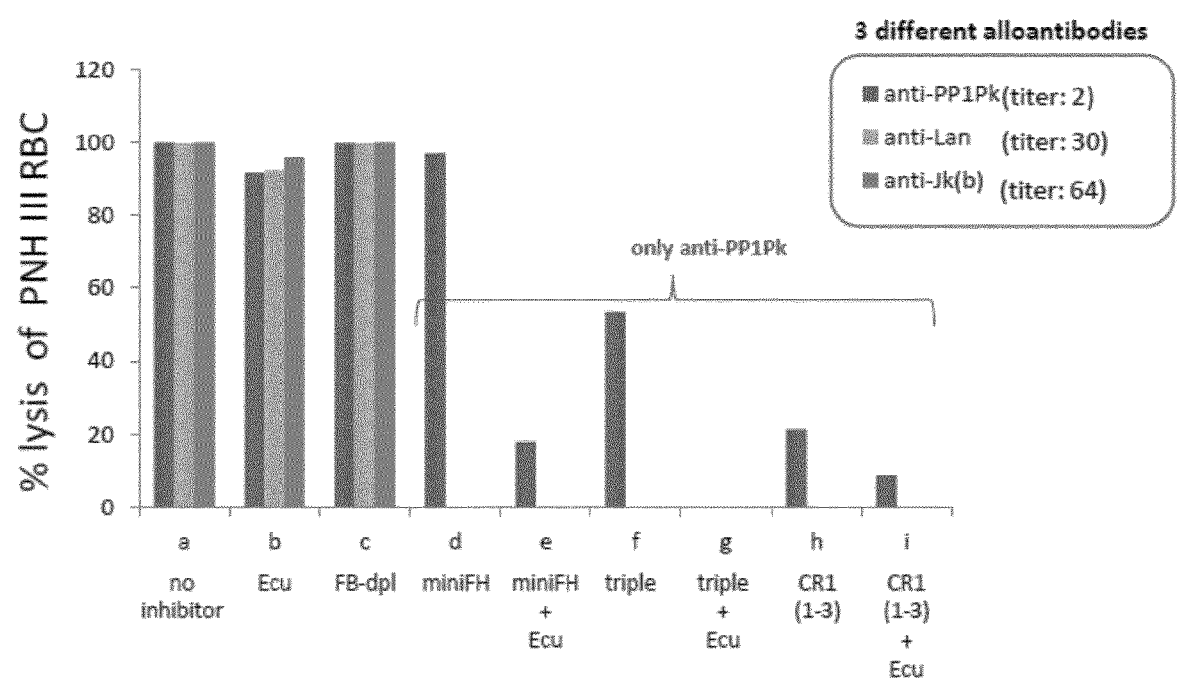

FIG. 5: Inhibition of classical pathway mediated hemolysis by combinations of inhibitors. x-axis: inhibitor (construct): a NHS; b NHS+eculizumab (1.2 μM); c FB depleted serum; d NHS+miniFH (=FH (1-4) FH (19-20), 2.5 μM); e NHS+mini FH (2.5 μM)+eculizumab (1.2 μM); f NHS+ triple I. (=DAF (1-4) FH (19-20) CR1 (15-17), 0.17 μM); g NHS+triple-I. (0.17 μM)+eculizumab (1.2 μM); h NHS+

CR1 (1-3) (7.3 μM); i NHS+CR1 (1-3) (7.3 μM)+eculizumab (1.2 μM) y-axis: lysis of PNH III RBC in %.

EXAMPLE 1: CONSTRUCTS

Nomenclature used: CR1 used in the examples was human CR1; FH relates to human complement Factor H, and DAF relates to human Decay Accelerating Factor. Numbers following abbreviations of protein names relate to the numbers of the CCPs within the protein used, e.g. FH (19-20) relates to CCPs 19 and 20 of Factor H.

The following constructs were used (FIG. 1): "DAF (1-4) FH (19-20) long linker" (SEQ ID NO: 11, encoded by SEQ ID NO:16), comprising an oligo-gly linker between DAF (1-4) and FH (19-20) (FIG. 1A); and "DAF (1-4) FH (19-20) short linker" (SEQ ID NO:12, encoded by SEQ ID NO:15), in which DAF (1-4) and FH (19-20) are directly connected, i.e. without linker. Constructs CR1 (1-3) FH (19-20) long linker (SEQ ID NO:9, encoded by SEQ ID NO: 18) and short linker (SEQ ID NO:10, encoded by SEQ ID NO:17) (FIG. 1B) were constructed analogously. Further, DAF (1-4) (soluble DAF, "sDAF", SEQ ID NO:2), CR1 (1-3) (SEQ ID NO:1), CR1 (15-17) (SEQ ID NO:3) were also used.

The coding DNAs for the multi-domain proteins "CR1 (1-3) FH (19-20) CR1 (15-17)" and "DAF (1-4) FH (19-20) CR1 (15-17)" were ordered (from Geneart) to be codon optimized for *Pichia pastoris* expression, synthesized and subcloned into the *Pichia pastoris* expression vector pPICZαB. CR1 (1-3) FH (19-20) CR1 (15-17) was encoded by SEQ ID NO:13; a polypeptide having the same amino acid sequence (SEQ ID NO:5) may, however, also be encoded by a polynucleotide comprising SEQ ID NO: 7. Also, DAF (1-4) FH (19-20) CR1 (15-17) was encoded by SEQ ID NO:14; a polypeptide having the same amino acid sequence (SEQ ID NO:6) may, however, also be encoded by a polynucleotide comprising SEQ ID NO: 8. The expression cassettes for all other constructs were prepared in the same vector background.

The respective proteins were overproduced in *P. pastoris* and were purified by conventional methods.

EXAMPLE 2: AFFINITY TO COMPLEMENT PROTEIN C3B

A surface plasmon resonance (SPR)-based assay (Schmidt et al. (2013), Journal of Immunology 190:5712-5721) was used to determine the affinity of the engineered complement inhibitors for the key complement protein C3b. 1940 response units (μRU) of C3b were coupled to the chip. The samples were run at 25 μl/min in a concentration series with the highest and the lowest concentrations being assayed in duplicate to probe reproducibility. To get an estimation of the KD value for other proteins the plot of response (during steady state) against the assayed concentration was fitted to a 1:1 steady state affinity model. The measured KD values for CR1 (15-17), DAF (1-4) and FH (19-20) were $K_D$=0.95 μM, $K_D$=11.5 μM and $K_D$=4.67 μM, respectively, and were in good agreement with the literature. Results are shown in Table 1.

TABLE 1

| Protein | KD values | Standard error of the fit in nM |
|---|---|---|
| CR1(1-3) | From literature: 38 μM | |
| CR1(15-17) | 0.954 μM | +/−2.40 |

TABLE 1-continued

| Protein | KD values | Standard error of the fit in nM |
|---|---|---|
| DAF(1-4) | 11.50 μM | +/−10.0 |
| FH(19-20) | 4.670 μM | +/−2.30 |
| CR1(1-3)FH(19-20)-SL | 1.650 μM | +/−0.70 |
| CR1(1-3)FH(19-20)-LL | 0.389 μM | +/−2.15 |
| DAF(1-4)FH(19-20)-SL | 0.125 μM | +/−0.07 |
| DAF(1-4)FH(19-20)-LL | 0.175 μM | +/−0.50 |
| CR1(1-3)FH(19-20)CR1(15-17) | 40.60 nM | +/−0.07 |
| DAF(1-4)FH(19-20)CR1(15-17) | 22.80 nM | +/−0.50 |

EXAMPLE 3: DECAY ACCELERATION ACTIVITY ASSAY

For measuring decay acceleration activity (DAA), also an established SPR-based assay (Schmidt et al. (2013), ibd.) was employed. 3653 μRUs of C3b were coupled to the chip surface. By flowing a mix of the purified proteins Factor B and Factor D (CompTech, USA) over the chip surface, Factor B binds to C3b thus enabling Factor D to cleave and activate Factor B. This results in formation of the AP convertase C3bBb on the chip. The bimolecular C3 convertase decays intrinsically at a slow rate, but upon exposure to a regulator with DAA the decay is dramatically accelerated. This setup was employed to test how efficiently the different fusion proteins can decay C3bBb. CR1 (15-17) was run as control, as it does not exhibit DAA, but only co-factor activity.

EXAMPLE 4: COFACTOR ASSAY

In order to verify that constructs that contain CR1 (15-17) have cofactor activity (CA), a CA assay was performed with the four analytes: CR1 (15-17), CR1 (1-3) FH (19-20) CR1 (15-17), DAF (1-4) FH (19-20) CR1 (15-17) and DAF (1-4) FH (19-20)-SL, which was included as a negative control. C3b alone were used as negative control.

C3b consists of two chains: the α- and the β-chain. In presence of a cofactor, Factor I inactivates C3b proteolytically to iC3b (or C3dg) by cleaving certain peptide bonds within the α'-chain of C3b. This activity/process can be easily monitored by SDS-PAGE analysis: The 113 kDa large α'-chain gets cleaved two times yielding three bands: the C3α'-68, -46 and -43 bands. The β-chain stays uncut. As expected the negative controls did not produce any cleavage of the α'-chain, but all fragments containing CR1 (15-17) exhibited CA.

EXAMPLE 5: ALTERNATIVE PATHWAY (AP)-SPECIFIC PROTECTION ASSAY OF RABBIT ERYTHROCYTES

To determine the ability of engineered complement regulators to specifically inhibit the AP activation pathway, a hemolysis assay of rabbit erythrocytes (RBCs) was performed. For this purpose, rabbit RBCs were incubated in 25% human serum that had been mixed with inhibitors and the following two reagents: To chelate specifically calcium ions and thus block any activity of the classical pathway (CP), EGTA was added. Magnesium ions were added to promote the activity of the AP, since the AP convertases depend on the presence of sufficient amounts of Mg-ions. Rabbit erythrocytes are known activators of the AP in human serum and are a good model system to probe AP activity. Initial C3 (H2O) and C3b deposition on the rabbit RBCs becomes quickly propagated via the AP amplification loop leading to the deposition of huge amounts of C3b and the formation of MAC and cell lysis. Unlike human RBCs, rabbit erythrocyte lack regulator proteins that can regulate the complement system present in human serum. As a consequence rabbit RBC get lysed and the level of lysis can be determined by measuring the release of hemoglobin (spectrophotometrically). By spiking in the complement regulatory proteins inhibition of the AP is achieved (by DAA and CA), which prevents C3b deposition and in consequence also MAC formation and lysis. Results are shown in FIG. 2, and in Table 2.

TABLE 2

| Engineered complement inhibitor | The lowest end concentration that prevents hemolysis in AP in µM |
|---|---|
| CR1(1-3) | 2.5 |
| CR1(15-17) | 0.625 |
| DAF(1-4) | 1.25 |
| CR1(1-3)FH(19-20)-SL | 0.625 |
| CR1(1-3)FH(19-20)-LL | 0.31 |
| DAF(1-4)FH(19-20)-SE | 0.625 |
| DAF(1-4)FH(19-20)-EE | 0.156 |
| CR1(1-3)FH(19-20) CR1(15-17) | 0.156 |
| DAF(1-4)FH(19-20) CR1(15-17) | 0.078 |

EXAMPLE 4: CLASSICAL PATHWAY (CP)-SPECIFIC PROTECTION ASSAY OF SENSITIZED SHEEP ERYTHROCYTES

To determine the ability of engineered complement regulators to inhibit the CP of complement system a hemolysis assay with sheep RBCs was performed. Sheep RBCs do not lyse readily in human serum because the sialic acid moieties on their surface recruit human FH and protect them from lysis by the AP. This situation is exploited and the sheep RBCs can be used to probe the CP of complement activation. Sheep erythrocytes are sensitized with an antibody against their surface before they are exposed to 5% human serum. Addition of magnesium and calcium ions ensures efficient functionality of the CP, which gets activated when the antibodies on the erythrocyte surface are sensed by the C1 complex. Activation leads to formation of C3-convertases, deposition of more and more C3b molecules and in the end formation of MAC and cell lysis. Since sheep RBCs have negatively charged sialic acid molecules on their surface, that means the can be partly targeted by FH (19-20). The engineered regulatory proteins were tested in this assay to probe their ability to inhibit the CP activation route. Results are shown in FIG. 3 and Table 3.

TABLE 3

| Engineered complement inhibitor | The lowest end concentration that prevents hemolysis in CP (5% serum) in µM |
|---|---|
| CR1(1-3) | 3 |
| CR1(15-17) | 17.7 |
| DAF(1-4) | 3 |
| CR1(1-3)FH(19-20)-SL | 0.83 |
| CR1(1-3)FH(19-20)-LL | 0.83 |
| DAF(1-4)FH(19-20)-SL | 0.27 |
| DAF(1-4)FH(19-20)-EL | 0.27 |
| CR1(1-3)FH(19-20) CR1(15-17) | 0.09 |
| DAF(1-4)FH(19-20) CR1(15-17) | 0.09 |

EXAMPLE 5: CLINICALLY RELEVANT EX VIVO MODEL OF AP-MEDIATED LYSIS OF PAROXYSMAL NOCTURNAL HEMOGLOBINURIA (PNH) ERYTHROCYTES

PNH erythrocytes from a PNH patient under Eculizumab treatment were used for this assay. ABO matched serum was used for the assay. ABO-matched RBCs from a healthy person were used as control. Two independent experiments were performed with data points being assayed in duplicates. Lysis of PNH erythrocytes was determined by measuring the hemoglobin release at an absorbance of 405 nm. To control that only/mainly PNH RBCs have lysed under the conditions assayed, the proportions of healthy cells (PNH type I cells), PNH type II and type III cells were measured (by FACS analysis) in a control sample in PBS in absence of serum (no lysis occurs) and for a sample that contained serum without the addition of an engineered inhibitor, which arbitrarily set the 100% value for PNH cell lysis. If the proportion of PNH II and III cells decreases during the serum incubation, it is indicative that indeed the vulnerably PNH II and III cells have lysed and contributed to the hemoglobin release (and not the healthy PNH type I cells). This indeed did occur, proving that the measuring of the absorbance at 405 nm indeed correlates with PNH III cell lysis. Results are shown in FIG. 4 and Table 4.

TABLE 4

| Engineered complement regulator | The lowest final concentration that prevents hemolysis of PNH RBCs (75% serum) in µM |
|---|---|
| CR1(1-3) | 3.2 |
| CR1(15-17) | 3.2 |
| DAF(1-4) | 1.6 |
| CR1(1-3)FH(19-20)-SL | 0.8 |
| CR1(1-3)FH(19-20)-LL | 0.2 |
| DAF(1-4)FH(19-20)-SL | 0.8 |
| DAF(1-4)FH(19-20)-EL | 0.4 |
| CR1(1-3)FH(19-20) CR1(15-17) | 0.2 |
| DAF(1-4)FH(19-20) CR1(15-17) | 0.2 |
| sCR1 | 0.8 |

EXAMPLE 6

When PNH erythrocytes were sensitized with alloantibodies against blood group antigens present on the PNH erythrocytes, the sensitized PNH erythrocytes lysed quickly in a complement dependent manner through CP activity that depended on the presence the alloantibodies. Even the presence of eculizumab, did not prevent hemolysis under these challenging condition with alloantibody. The PNH erythrocytes were used in this CP assay to have a human cell (instead of sheep erythrocytes) for the experiment that are complement sensitive. Also healthy erythrocytes could have been used, but the experimental readout (i.e. the detection of complement activity would have been harder to obtain). The result shown in FIG. 5 were obtained. Unexpectedly, eculizumab at 1.2 µM (which is 5-fold above the C5 concentration in the assay) does not inhibit lysis after forceful CP activation; as expected, miniFH (at 2.5 µM which is 10-fold above the efficient conc. that inhibits the AP) does not inhibit CP-mediated lysis; DAF (1-4) FH19-20CR1 (15-17), referred to as "triple I" in FIG. 5, at 0.17 µM does inhibit part of the hemolysis; CR1 (1-3) at 7.3 µM does inhibit part of the hemolysis; thus, DAF (1-4) FH19-20CR1 (15-17) is much more effective than CR1 (1-3) (40-fold difference in activity) or Eculizumab alone.

The invention claimed is:

1. A multi-domain polypeptide comprising:

(i) a first complement control protein repeat (CCP) comprising domain comprising multiple CCPs, wherein the multiple CCPs consist of CCPs 1 to 3 of a complement receptor type 1 (CR1); and/or CCPs 1 to 4 of a decay accelerating factor (DAF), wherein the first CCP comprising domain is a convertase decay accelerating domain for convertases of the classical and alternative pathways of complement activation;

(ii) a host cell recognition domain comprising multiple CCPs, wherein the multiple CCPs consist of CCPs 6 to 8 and/or CCPs 19 to 20 of a complement Factor H; and (iii) a second CCP-comprising domain comprising multiple CCPs, wherein the multiple CCPs consist of CCPs 8 to 10 and/or 15 to 17 of CR1, wherein said multi-domain polypeptide comprises an amino acid sequence at least 95% identical to SEQ ID NO: 5 or 6.

2. The multi-domain polypeptide of claim 1, wherein said first CCP-comprising domain comprises an amino acid sequence as shown in SEQ ID NO:1 or an amino acid sequence being at least 95% identical to SEQ ID NO:1.

3. The multi-domain polypeptide of claim 1, wherein said first CCP-comprising domain comprises an amino acid sequence as shown in SEQ ID NO:2 or an amino acid sequence being at least 95% identical to SEQ ID NO:2.

4. The multi-domain polypeptide of claim 1, wherein said second CCP-comprising domain comprises an amino acid sequence as shown in SEQ ID NO:3 or an amino acid sequence being at least 95% identical to SEQ ID NO:3.

5. The multi-domain polypeptide of claim 1, wherein said host cell recognition domain comprises an amino acid sequence as shown in SEQ ID NO:4 or an amino acid sequence being at least 95% identical to SEQ ID NO:4.

6. The multi-domain polypeptide of claim 1, wherein said first CCP-comprising domain comprises at least one CCPs having binding activity for complement factors C3b and C4b.

7. The multi-domain polypeptide of claim 1, wherein said second CCP-comprising domain comprises at least one CCPs having binding activity for complement factors C3b and/or C4b.

8. The multi-domain polypeptide of claim 1, wherein said host cell recognition domain comprises at least one CCPs having binding activity to complement factor C3b degradation products; and/or having binding activity to host cell surface markers.

9. The multi-domain polypeptide of claim 1, wherein said multi-domain polypeptide has the activity of inhibiting at least two activation pathways of the complement system.

10. A combined preparation for simultaneous, separate or sequential use comprising (i) a multi-domain polypeptide according to claim 1 and (ii) a complement protein C5 inhibiting polypeptide.

11. A method for preventing or reducing the degree of complement activation comprising applying a multi-domain polypeptide according to claim 1 to a reaction mixture comprising complement factors, thereby preventing or reducing the degree of complement activation in said reaction mixture.

* * * * *

SEQUENCE LISTING

<160> NUMBER OF SEQ ID NOS: 18

<210> SEQ ID NO 1
<211> LENGTH: 193
<212> TYPE: PRT
<213> ORGANISM: Homo sapiens

<400> SEQUENCE: 1

Gln Cys Asn Ala Pro Glu Trp Leu Pro Phe Ala Arg Pro Thr Gln Leu
1               5                   10                  15

Thr Asp Glu Phe Glu Phe Pro Ile Gly Thr Tyr Leu Asn Tyr Glu Cys
            20                  25                  30

Arg Pro Gly Tyr Ser Gly Arg Pro Phe Ser Ile Ile Cys Leu Lys Asn
        35                  40                  45

Ser Val Trp Thr Gly Ala Lys Asp Arg Cys Arg Arg Lys Ser Cys Arg
50                  55                  60

Asn Pro Pro Asp Pro Val Asn Gly Met Val His Val Ile Lys Gly Ile
65                  70                  75                  80

Gln Phe Gly Ser Gln Ile Lys Tyr Ser Cys Thr Lys Gly Tyr Arg Leu
                85                  90                  95

Ile Gly Ser Ser Ser Ala Thr Cys Ile Ile Ser Gly Asp Thr Val Ile
            100                 105                 110

Trp Asp Gln Glu Thr Pro Ile Cys Asp Arg Ile Pro Cys Gly Leu Pro
        115                 120                 125

Pro Thr Ile Thr Asn Gly Asp Phe Ile Ser Thr Asn Arg Glu Asn Phe
130                 135                 140

His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
            180                 185                 190

Ile

<210> SEQ ID NO 2
<211> LENGTH: 250
<212> TYPE: PRT
<213> ORGANISM: Homo sapiens

<400> SEQUENCE: 2

Asp Cys Gly Leu Pro Pro Asp Val Pro Asn Ala Gln Pro Ala Leu Glu
1               5                   10                  15

Gly Arg Thr Ser Phe Pro Glu Asp Thr Val Ile Thr Tyr Lys Cys Glu
            20                  25                  30

Glu Ser Phe Val Lys Ile Pro Gly Glu Lys Asp Ser Val Ile Cys Leu
        35                  40                  45

Lys Gly Ser Gln Trp Ser Asp Ile Glu Glu Phe Cys Gln Arg Ser Cys
50                  55                  60

Glu Val Pro Thr Arg Leu Asn Ser Ala Ser Leu Lys Gln Pro Tyr Ile
65                  70                  75                  80

Thr Gln Asn Tyr Phe Pro Val Gly Thr Val Val Glu Tyr Glu Cys Arg
                85                  90                  95

Pro Gly Tyr Arg Arg Glu Pro Ser Leu Ser Pro Lys Leu Thr Cys Leu
            100                 105                 110

```
Gln Asn Leu Lys Trp Ser Thr Ala Val Glu Phe Cys Lys Lys Ser
            115                 120                 125
Cys Pro Asn Pro Gly Glu Ile Arg Asn Gly Gln Ile Asp Val Pro Gly
130                 135                 140
Gly Ile Leu Phe Gly Ala Thr Ile Ser Phe Ser Cys Asn Thr Gly Tyr
145                 150                 155                 160
Lys Leu Phe Gly Ser Thr Ser Ser Phe Cys Leu Ile Ser Gly Ser Ser
                165                 170                 175
Val Gln Trp Ser Asp Pro Leu Pro Glu Cys Arg Glu Ile Tyr Cys Pro
            180                 185                 190
Ala Pro Pro Gln Ile Asp Asn Gly Ile Ile Gln Gly Glu Arg Asp His
            195                 200                 205
Tyr Gly Tyr Arg Gln Ser Val Thr Tyr Ala Cys Asn Lys Gly Phe Thr
            210                 215                 220
Met Ile Gly Glu His Ser Ile Tyr Cys Thr Val Asn Asn Asp Glu Gly
225                 230                 235                 240
Glu Trp Ser Gly Pro Pro Glu Cys Arg
                245                 250

<210> SEQ ID NO 3
<211> LENGTH: 194
<212> TYPE: PRT
<213> ORGANISM: Homo sapiens

<400> SEQUENCE: 3

Gly His Cys Gln Ala Pro Asp His Phe Leu Phe Ala Lys Leu Lys Thr
1               5                   10                  15
Gln Thr Gln Ala Ser Asp Phe Pro Ile Gly Thr Ser Leu Lys Tyr Glu
            20                  25                  30
Cys Arg Pro Glu Tyr Tyr Gly Arg Pro Phe Ser Ile Thr Cys Leu Asp
        35                  40                  45
Asn Leu Val Trp Ser Ser Pro Lys Asp Val Cys Lys Arg Lys Ser Cys
    50                  55                  60
Lys Thr Pro Pro Asp Pro Val Asn Gly Met Val His Val Ile Thr Asp
65                  70                  75                  80
Ile Gln Val Gly Ser Arg Ile Gln Tyr Ser Cys Thr Thr Gly His Arg
                85                  90                  95
Leu Ile Gly His Ser Ser Ala Glu Cys Ile Leu Ser Gly Asn Thr Ala
            100                 105                 110
His Trp Ser Thr Lys Pro Pro Ile Cys Gln Arg Ile Pro Cys Gly Leu
            115                 120                 125
Pro Pro Thr Ile Ala Asn Gly Asp Phe Ile Ser Thr Asn Arg Glu Asn
            130                 135                 140
Phe His Tyr Gly Ser Val Val Thr Tyr Arg Cys Asn Leu Gly Ser Arg
145                 150                 155                 160
Gly Arg Lys Val Phe Glu Leu Val Gly Glu Pro Ser Ile Tyr Cys Thr
                165                 170                 175
Ser Asn Asp Asp Gln Val Gly Ile Trp Ser Gly Pro Ala Pro Gln Cys
            180                 185                 190
Ile Ile

<210> SEQ ID NO 4
<211> LENGTH: 122
<212> TYPE: PRT
<213> ORGANISM: Homo sapiens
```

<400> SEQUENCE: 4

```
Lys Cys Gly Pro Pro Pro Ile Asp Asn Gly Asp Ile Thr Ser Phe
1               5                   10                  15

Pro Leu Ser Val Tyr Ala Pro Ala Ser Ser Val Glu Tyr Gln Cys Gln
            20                  25                  30

Asn Leu Tyr Gln Leu Glu Gly Asn Lys Arg Ile Thr Cys Arg Asn Gly
            35                  40                  45

Gln Trp Ser Glu Pro Pro Lys Cys Leu His Pro Cys Val Ile Ser Arg
    50                  55                  60

Glu Ile Met Glu Asn Tyr Asn Ile Ala Leu Arg Trp Thr Ala Lys Gln
65              70                  75                  80

Lys Leu Tyr Ser Arg Thr Gly Glu Ser Val Glu Phe Val Cys Lys Arg
                85                  90                  95

Gly Tyr Arg Leu Ser Ser Arg Ser His Thr Leu Arg Thr Thr Cys Trp
                100                 105                 110

Asp Gly Lys Leu Glu Tyr Pro Thr Cys Ala
                115                 120
```

<210> SEQ ID NO 5
<211> LENGTH: 529
<212> TYPE: PRT
<213> ORGANISM: Artificial
<220> FEATURE:
<223> OTHER INFORMATION: artificial multi-domain polypeptide,
      CR1-derived first CCP domain

<400> SEQUENCE: 5

```
Gln Cys Asn Ala Pro Glu Trp Leu Pro Phe Ala Arg Pro Thr Gln Leu
1               5                   10                  15

Thr Asp Glu Phe Glu Phe Pro Ile Gly Thr Tyr Leu Asn Tyr Glu Cys
            20                  25                  30

Arg Pro Gly Tyr Ser Gly Arg Pro Phe Ser Ile Ile Cys Leu Lys Asn
            35                  40                  45

Ser Val Trp Thr Gly Ala Lys Asp Arg Cys Arg Arg Lys Ser Cys Arg
    50                  55                  60

Asn Pro Pro Asp Pro Val Asn Gly Met Val His Val Ile Lys Gly Ile
65              70                  75                  80

Gln Phe Gly Ser Gln Ile Lys Tyr Ser Cys Thr Lys Gly Tyr Arg Leu
                85                  90                  95

Ile Gly Ser Ser Ser Ala Thr Cys Ile Ile Ser Gly Asp Thr Val Ile
                100                 105                 110

Trp Asp Gln Glu Thr Pro Ile Cys Asp Arg Ile Pro Cys Gly Leu Pro
                115                 120                 125

Pro Thr Ile Thr Asn Gly Asp Phe Ile Ser Thr Asn Arg Glu Asn Phe
            130                 135                 140

His Tyr Gly Ser Val Val Thr Tyr Arg Cys Asn Pro Gly Ser Gly Gly
145             150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
                180                 185                 190

Ile Gly Gly Gly Gly Gly Gly Gly Gly Gly Gly Gly Gly Gly Gly Lys
                195                 200                 205

Cys Gly Pro Pro Pro Ile Asp Asn Gly Asp Ile Thr Ser Phe Pro
                210                 215                 220
```

```
Leu Ser Val Tyr Ala Pro Ala Ser Ser Val Glu Tyr Gln Cys Gln Asn
225                 230                 235                 240

Leu Tyr Gln Leu Glu Gly Asn Lys Arg Ile Thr Cys Arg Asn Gly Gln
            245                 250                 255

Trp Ser Glu Pro Pro Lys Cys Leu His Pro Cys Val Ile Ser Arg Glu
        260                 265                 270

Ile Met Glu Asn Tyr Asn Ile Ala Leu Arg Trp Thr Ala Lys Gln Lys
    275                 280                 285

Leu Tyr Ser Arg Thr Gly Glu Ser Val Glu Phe Val Cys Lys Arg Gly
290                 295                 300

Tyr Arg Leu Ser Ser Arg Ser His Thr Leu Arg Thr Cys Trp Asp
305                 310                 315                 320

Gly Lys Leu Glu Tyr Pro Thr Cys Ala Gly Gly Gly Gly Gly Gly
            325                 330                 335

His Cys Gln Ala Pro Asp His Phe Leu Phe Ala Lys Leu Lys Thr Gln
        340                 345                 350

Thr Gln Ala Ser Asp Phe Pro Ile Gly Thr Ser Leu Lys Tyr Glu Cys
    355                 360                 365

Arg Pro Glu Tyr Tyr Gly Arg Pro Phe Ser Ile Thr Cys Leu Asp Asn
370                 375                 380

Leu Val Trp Ser Ser Pro Lys Asp Val Cys Lys Arg Lys Ser Cys Lys
385                 390                 395                 400

Thr Pro Pro Asp Pro Val Asn Gly Met Val His Val Ile Thr Asp Ile
            405                 410                 415

Gln Val Gly Ser Arg Ile Gln Tyr Ser Cys Thr Thr Gly His Arg Leu
        420                 425                 430

Ile Gly His Ser Ser Ala Glu Cys Ile Leu Ser Gly Asn Thr Ala His
    435                 440                 445

Trp Ser Thr Lys Pro Pro Ile Cys Gln Arg Ile Pro Cys Gly Leu Pro
450                 455                 460

Pro Thr Ile Ala Asn Gly Asp Phe Ile Ser Thr Asn Arg Glu Asn Phe
465                 470                 475                 480

His Tyr Gly Ser Val Val Thr Tyr Arg Cys Asn Leu Gly Ser Arg Gly
            485                 490                 495

Arg Lys Val Phe Glu Leu Val Gly Glu Pro Ser Ile Tyr Cys Thr Ser
        500                 505                 510

Asn Asp Asp Gln Val Gly Ile Trp Ser Gly Pro Ala Pro Gln Cys Ile
    515                 520                 525

Ile

<210> SEQ ID NO 6
<211> LENGTH: 587
<212> TYPE: PRT
<213> ORGANISM: Artificial
<220> FEATURE:
<223> OTHER INFORMATION: artificial multi-domain polypeptide,
      DAF-derived first CCP domain

<400> SEQUENCE: 6

Asp Cys Gly Leu Pro Pro Asp Val Pro Asn Ala Gln Pro Ala Leu Glu
1               5                   10                  15

Gly Arg Thr Ser Phe Pro Glu Asp Thr Val Ile Thr Tyr Lys Cys Glu
            20                  25                  30

Glu Ser Phe Val Lys Ile Pro Gly Glu Lys Asp Ser Val Ile Cys Leu
        35                  40                  45
```

```
Lys Gly Ser Gln Trp Ser Asp Ile Glu Glu Phe Cys Gln Arg Ser Cys
 50                  55                  60

Glu Val Pro Thr Arg Leu Asn Ser Ala Ser Leu Lys Gln Pro Tyr Ile
 65                  70                  75                  80

Thr Gln Asn Tyr Phe Pro Val Gly Thr Val Val Glu Tyr Glu Cys Arg
                     85                  90                  95

Pro Gly Tyr Arg Arg Glu Pro Ser Leu Ser Pro Lys Leu Thr Cys Leu
                100                 105                 110

Gln Asn Leu Lys Trp Ser Thr Ala Val Glu Phe Cys Lys Lys Lys Ser
            115                 120                 125

Cys Pro Asn Pro Gly Glu Ile Arg Asn Gly Gln Ile Asp Val Pro Gly
130                 135                 140

Gly Ile Leu Phe Gly Ala Thr Ile Ser Phe Ser Cys Asn Thr Gly Tyr
145                 150                 155                 160

Lys Leu Phe Gly Ser Thr Ser Ser Phe Cys Leu Ile Ser Gly Ser Ser
                165                 170                 175

Val Gln Trp Ser Asp Pro Leu Pro Glu Cys Arg Glu Ile Tyr Cys Pro
            180                 185                 190

Ala Pro Pro Gln Ile Asp Asn Gly Ile Ile Gln Gly Glu Arg Asp His
            195                 200                 205

Tyr Gly Tyr Arg Gln Ser Val Thr Tyr Ala Cys Asn Lys Gly Phe Thr
210                 215                 220

Met Ile Gly Glu His Ser Ile Tyr Cys Thr Val Asn Asn Asp Glu Gly
225                 230                 235                 240

Glu Trp Ser Gly Pro Pro Glu Cys Arg Gly Gly Gly Gly Gly Gly Gly
                245                 250                 255

Gly Gly Gly Gly Gly Gly Gly Gly Lys Cys Gly Pro Pro Pro
                260                 265                 270

Ile Asp Asn Gly Asp Ile Thr Ser Phe Pro Leu Ser Val Tyr Ala Pro
            275                 280                 285

Ala Ser Ser Val Glu Tyr Gln Cys Gln Asn Leu Tyr Gln Leu Glu Gly
            290                 295                 300

Asn Lys Arg Ile Thr Cys Arg Asn Gly Gln Trp Ser Glu Pro Pro Lys
305                 310                 315                 320

Cys Leu His Pro Cys Val Ile Ser Arg Glu Ile Met Glu Asn Tyr Asn
                325                 330                 335

Ile Ala Leu Arg Trp Thr Ala Lys Gln Lys Leu Tyr Ser Arg Thr Gly
                340                 345                 350

Glu Ser Val Glu Phe Val Cys Lys Arg Gly Tyr Arg Leu Ser Ser Arg
            355                 360                 365

Ser His Thr Leu Arg Thr Thr Cys Trp Asp Gly Lys Leu Glu Tyr Pro
            370                 375                 380

Thr Cys Ala Gly Gly Gly Gly Gly Gly His Cys Gln Ala Pro Asp
385                 390                 395                 400

His Phe Leu Phe Ala Lys Leu Lys Thr Gln Thr Gln Ala Ser Asp Phe
                405                 410                 415

Pro Ile Gly Thr Ser Leu Lys Tyr Glu Cys Arg Pro Glu Tyr Tyr Gly
                420                 425                 430

Arg Pro Phe Ser Ile Thr Cys Leu Asp Asn Leu Val Trp Ser Ser Pro
            435                 440                 445

Lys Asp Val Cys Lys Arg Lys Ser Cys Lys Thr Pro Pro Asp Pro Val
450                 455                 460
```

```
Asn Gly Met Val His Val Ile Thr Asp Ile Gln Val Gly Ser Arg Ile
465                 470                 475                 480

Gln Tyr Ser Cys Thr Thr Gly His Arg Leu Ile Gly His Ser Ser Ala
            485                 490                 495

Glu Cys Ile Leu Ser Gly Asn Thr Ala His Trp Ser Thr Lys Pro Pro
        500                 505                 510

Ile Cys Gln Arg Ile Pro Cys Gly Leu Pro Pro Thr Ile Ala Asn Gly
    515                 520                 525

Asp Phe Ile Ser Thr Asn Arg Glu Asn Phe His Tyr Gly Ser Val Val
530                 535                 540

Thr Tyr Arg Cys Asn Leu Gly Ser Arg Gly Arg Lys Val Phe Glu Leu
545                 550                 555                 560

Val Gly Glu Pro Ser Ile Tyr Cys Thr Ser Asn Asp Asp Gln Val Gly
            565                 570                 575

Ile Trp Ser Gly Pro Ala Pro Gln Cys Ile Ile
            580                 585
```

<210> SEQ ID NO 7
<211> LENGTH: 1587
<212> TYPE: DNA
<213> ORGANISM: Artificial
<220> FEATURE:
<223> OTHER INFORMATION: artificial multi-domain polypeptide encoding sequence, CR1-derived first CCP domain

<400> SEQUENCE: 7

```
cagtgcaacg cgccggaatg gctgccgttt gcgcgcccga cccagctgac cgatgaattt      60
gaatttccga ttggcaccta tctgaactat gaatgccgcc cgggctatag cggccgcccg     120
tttagcatta tttgcctgaa aaacagcgtg tggaccggcg cgaaagatcg ctgccgccgc     180
aaaagctgcc gcaacccgcc ggatccggtg aacggcatgg tgcatgtgat taaaggcatt     240
cagtttggca gccagattaa atatagctgc accaaaggct atcgcctgat tggcagcagc     300
agcgcgacct gcattattag cggcgatacc gtgatttggg atcaggaaac cccgatttgc     360
gatcgcattc cgtgcggcct gccgccgacc attaccaacg gcgattttat tagcaccaac     420 cgcgaaaaact ttcattatgg cagcgtggtg acctatcgct gcaacccggg cagcggcggc     480
cgcaaagtgt ttgaactggt gggcgaaccg agcatttatt gcaccagcaa cgatgatcag     540
gtgggcattt ggagcggccc ggcgccgcag tgcattattg cggcggcggc ggcggcggcg     600 gcggcggcg gcggcggcgg caaatgcggc ccgccgccgc cgattgataa cggcgatatt     660
accagctttc cgctgagcgt gtatgcgccg gcgagcagcg tggaatatca gtgccagaac     720
ctgtatcagc tggaaggcaa caaacgcatt acctgccgca acggccagtg gagcgaaccg     780
ccgaaatgcc tgcatccgtg cgtgattagc cgcgaaatta tggaaaacta taacattgcg     840
ctgcgctgga ccgcgaaaca gaaactgtat agccgcaccg gcgaaagcgt ggaatttgtg     900
tgcaaacgcg gctatcgcct gagcagccgc agccataccc tgcgcaccac ctgctgggat     960
ggcaaactgg aatatccgac ctgcgcgggc ggcggcggcg gcggcggcca ttgccaggcg    1020
ccggatcatt ttctgtttgc gaaactgaaa acccagaccc aggcgagcga ttttccgatt    1080
ggcaccagcc tgaaatatga atgccgcccg gaatattatg gccgcccgtt tagcattacc    1140
tgcctggata acctggtgtg gagcagcccg aaagatgtgt gcaaacgcaa aagctgcaaa    1200
accccgccgg atccggtgaa cggcatggtg catgtgatta ccgatattca ggtgggcagc    1260
cgcattcagt atagctgcac caccggccat cgcctgattg gccatagcag cgcggaatgc    1320
```

```
attctgagcg gcaacaccgc gcattggagc accaaaccgc cgatttgcca gcgcattccg   1380
tgcggcctgc cgccgaccat tgcgaacggc gatttttatta gcaccaaccg cgaaaacttt   1440
cattatggca gcgtggtgac ctatcgctgc aacctgggca gccgcggccg caaagtgttt   1500
gaactggtgg cgaaccgag catttattgc accagcaacg atgatcaggt gggcatttgg   1560
agcggcccgg cgccgcagtg cattatt                                       1587
```

<210> SEQ ID NO 8
<211> LENGTH: 1761
<212> TYPE: DNA
<213> ORGANISM: Artificial
<220> FEATURE:
<223> OTHER INFORMATION: artificial multi-domain polypeptide encoding
      sequence, DAF-derived first CCP domain

<400> SEQUENCE: 8

```
gattgcggcc tgccgccgga tgtgccgaac gcgcagccgg cgctggaagg ccgcaccagc    60
tttccggaag ataccgtgat tacctataaa tgcgaagaaa gctttgtgaa aattccgggc   120
gaaaaagata gcgtgatttg cctgaaaggc agccagtgga gcgatattga agaattttgc   180
cagcgcagct gcgaagtgcc gacccgcctg aacagcgcga gcctgaaaca gccgtatatt   240
acccagaact atttccggt gggcaccgtg gtggaatatg aatgccgccc gggctatcgc   300
cgcgaaccga gcctgagccc gaaactgacc tgcctgcaga acctgaaatg gagcaccgcg   360 gtggaattt gcaaaaaaaa aagctgcccg aacccgggcg aaattcgcaa cggccagatt   420
gatgtgccgg cggcattct gtttggcgcg accattagct ttagctgcaa caccggctat   480
aaactgtttg cagcaccag cagcttttgc ctgattagcg gcagcagcgt gcagtggagc   540
gatccgctgc cggaatgccg cgaaatttat tgcccggcgc cgccgcagat tgataacggc   600
attattcagg gcgaacgcga tcattatggc tatcgccaga gcgtgaccta tcgtgcaac   660 aaaggcttta ccatgattgg cgaacatagc atttattgca ccgtgaacaa cgatgaaggc   720
gaatggagcg gcccgccgcc ggaatgccgc ggcggcggcg gcggcggcgg cggcggcggc   780
ggcggcggcg gcgcaaatg cggcccgccg ccgccgattg ataacggcga tattaccagc   840
tttccgctga gcgtgtatgc gccggcgagc agcgtgaat atcagtgcca gaacctgtat   900
cagctggaag gcaacaaacg cattacctgc cgcaacggcc agtggagcga accgccgaaa   960
tgcctgcatc cgtgcgtgat tagccgcgaa attatgaaa actataacat tgcgctgcgc  1020
tggaccgcga aacagaaact gtatagccgc accggcgaaa gcgtggaatt tgtgtgcaaa  1080
cgcggctatc gcctgagcag ccgcagccat accctgcgca ccacctgctg ggatggcaaa  1140
ctggaatatc cgacctgcgc gggcggcggc ggcggcggcg gccattgcca ggcgccggat  1200 catttctgt ttgcgaaact gaaaacccag acccaggcga cgattttcc gattggcacc  1260 agcctgaaat atgaatgccg cccggaatat tatggccgcc cgtttagcat tacctgcctg  1320
gataacctgg tgtggagcag cccgaaagat gtgtgcaaac gcaaaagctg caaaacccg  1380 ccggatccgg tgaacggcat ggtgcatgtg attaccgata ttcaggtggg cagccgcatt  1440
cagtatagct gcaccaccgg ccatcgcctg attggccata gcagcgcgga atgcattctg  1500
agcggcaaca ccgcgcattg gagcaccaaa ccgccgattt gccagcgcat tccgtgcggc  1560
ctgccgccga ccattgcgaa cggcgatttt attagcacca accgcgaaaa ctttcattat  1620
ggcagcgtgg tgacctatcg ctgcaacctg ggcagccgcg gccgcaaagt gtttgaactg  1680
gtgggcgaac cgagcattta ttgcaccagc aacgatgatc aggtgggcat ttggagcggc  1740
```
ccggcgccgc agtgcattat t                                                    1761

<210> SEQ ID NO 9
<211> LENGTH: 329
<212> TYPE: PRT
<213> ORGANISM: Artificial
<220> FEATURE:
<223> OTHER INFORMATION: CR1(1-3)FH(19-20) long linker polypeptide

<400> SEQUENCE: 9

Gln Cys Asn Ala Pro Glu Trp Leu Pro Phe Ala Arg Pro Thr Gln Leu
1               5                   10                  15

Thr Asp Glu Phe Glu Phe Pro Ile Gly Thr Tyr Leu Asn Tyr Glu Cys
            20                  25                  30

Arg Pro Gly Tyr Ser Gly Arg Pro Phe Ser Ile Ile Cys Leu Lys Asn
        35                  40                  45

Ser Val Trp Thr Gly Ala Lys Asp Arg Cys Arg Arg Lys Ser Cys Arg
    50                  55                  60

Asn Pro Pro Asp Pro Val Asn Gly Met Val His Val Ile Lys Gly Ile
65                  70                  75                  80

Gln Phe Gly Ser Gln Ile Lys Tyr Ser Cys Thr Lys Gly Tyr Arg Leu
                85                  90                  95

Ile Gly Ser Ser Ser Ala Thr Cys Ile Ile Ser Gly Asp Thr Val Ile
            100                 105                 110

Trp Asp Gln Glu Thr Pro Ile Cys Asp Arg Ile Pro Cys Gly Leu Pro
        115                 120                 125

Pro Thr Ile Thr Asn Gly Asp Phe Ile Ser Thr Asn Arg Glu Asn Phe
130                 135                 140

His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
            180                 185                 190

Ile Gly Gly Gly Gly Gly Gly Gly Gly Gly Gly Gly Gly Gly Gly Lys
        195                 200                 205

Cys Gly Pro Pro Pro Pro Ile Asp Asn Gly Asp Ile Thr Ser Phe Pro
210                 215                 220

Leu Ser Val Tyr Ala Pro Ala Ser Ser Val Glu Tyr Gln Cys Gln Asn
225                 230                 235                 240

Leu Tyr Gln Leu Glu Gly Asn Lys Arg Ile Thr Cys Arg Asn Gly Gln
                245                 250                 255

Trp Ser Glu Pro Pro Lys Cys Leu His Pro Cys Val Ile Ser Arg Glu
            260                 265                 270

Ile Met Glu Asn Tyr Asn Ile Ala Leu Arg Trp Thr Ala Lys Gln Lys
        275                 280                 285

Leu Tyr Ser Arg Thr Gly Glu Ser Val Glu Phe Val Cys Lys Arg Gly
    290                 295                 300

Tyr Arg Leu Ser Ser Arg Ser His Thr Leu Arg Thr Thr Cys Trp Asp
305                 310                 315                 320

Gly Lys Leu Glu Tyr Pro Thr Cys Ala
                325

<210> SEQ ID NO 10
<211> LENGTH: 321
<212> TYPE: PRT

<213> ORGANISM: Artificial
<220> FEATURE:
<223> OTHER INFORMATION: CR1(1-3)FH(19-20)short linker polypeptide

<400> SEQUENCE: 10

```
Gln Cys Asn Ala Pro Glu Trp Leu Pro Phe Ala Arg Pro Thr Gln Leu
1               5                   10                  15

Thr Asp Glu Phe Glu Phe Pro Ile Gly Thr Tyr Leu Asn Tyr Glu Cys
            20                  25                  30

Arg Pro Gly Tyr Ser Gly Arg Pro Phe Ser Ile Ile Cys Leu Lys Asn
        35                  40                  45

Ser Val Trp Thr Gly Ala Lys Asp Arg Cys Arg Arg Lys Ser Cys Arg
    50                  55                  60

Asn Pro Pro Asp Pro Val Asn Gly Met Val His Val Ile Lys Gly Ile
65              70                  75                  80

Gln Phe Gly Ser Gln Ile Lys Tyr Ser Cys Thr Lys Gly Tyr Arg Leu
            85                  90                  95

Ile Gly Ser Ser Ser Ala Thr Cys Ile Ile Ser Gly Asp Thr Val Ile
        100                 105                 110

Trp Asp Gln Glu Thr Pro Ile Cys Asp Arg Ile Pro Cys Gly Leu Pro
    115                 120                 125

Pro Thr Ile Ala Asn Gly Asp Phe Ile Ser Thr Asn Arg Glu Asn Phe
130             135                 140

His Tyr Gly Ser Val Val Thr Tyr Arg Cys Asn Pro Gly Ser Gly Gly
145             150                 155                 160

Arg Lys Val Phe Glu Leu Val Gly Glu Pro Ser Ile Tyr Cys Thr Ser
            165                 170                 175

Asn Asp Asp Gln Val Gly Ile Trp Ser Gly Pro Ala Pro Gln Cys Ile
        180                 185                 190

Ile Gly Pro Gly Gly Lys Cys Gly Pro Pro Pro Ile Asp Asn Gly
        195                 200                 205

Asp Ile Thr Ser Phe Pro Leu Ser Val Tyr Ala Pro Ala Ser Ser Val
        210                 215                 220

Glu Tyr Gln Cys Gln Asn Leu Tyr Gln Leu Glu Gly Asn Lys Arg Ile
225             230                 235                 240

Thr Cys Arg Asn Gly Gln Trp Ser Glu Pro Pro Lys Cys Leu His Pro
            245                 250                 255

Cys Val Ile Ser Arg Glu Ile Met Glu Asn Tyr Asn Ile Ala Leu Arg
        260                 265                 270

Trp Thr Ala Lys Gln Lys Leu Tyr Ser Arg Thr Gly Glu Ser Val Glu
        275                 280                 285

Phe Val Cys Lys Arg Gly Tyr Arg Leu Ser Ser Arg Ser His Thr Leu
290             295                 300

Arg Thr Thr Cys Trp Asp Gly Lys Leu Glu Tyr Pro Thr Cys Ala Lys
305             310                 315                 320

Arg
```

<210> SEQ ID NO 11
<211> LENGTH: 387
<212> TYPE: PRT
<213> ORGANISM: Artificial
<220> FEATURE:
<223> OTHER INFORMATION: DAF(1-4)FH(19-20) long linker polypeptide

<400> SEQUENCE: 11

Asp Cys Gly Leu Pro Pro Asp Val Pro Asn Ala Gln Pro Ala Leu Glu

```
              1               5                    10                   15
            Gly Arg Thr Ser Phe Pro Glu Asp Thr Val Ile Thr Tyr Lys Cys Glu
                            20                  25                  30

Glu Ser Phe Val Lys Ile Pro Gly Glu Lys Asp Ser Val Ile Cys Leu
                            35                  40                  45

Lys Gly Ser Gln Trp Ser Asp Ile Glu Glu Phe Cys Gln Arg Ser Cys
             50                  55                  60

Glu Val Pro Thr Arg Leu Asn Ser Ala Ser Leu Lys Gln Pro Tyr Ile
             65                  70                  75                  80

Thr Gln Asn Tyr Phe Pro Val Gly Thr Val Glu Tyr Glu Cys Arg
                            85                  90                  95

Pro Gly Tyr Arg Arg Glu Pro Ser Leu Ser Pro Lys Leu Thr Cys Leu
                            100                 105                 110

Gln Asn Leu Lys Trp Ser Thr Ala Val Glu Phe Cys Lys Lys Ser
                            115                 120                 125

Cys Pro Asn Pro Gly Glu Ile Arg Asn Gly Gln Ile Asp Val Pro Gly
                            130                 135                 140

Gly Ile Leu Phe Gly Ala Thr Ile Ser Phe Ser Cys Asn Thr Gly Tyr
            145                 150                 155                 160

Lys Leu Phe Gly Ser Thr Ser Ser Phe Cys Leu Ile Ser Gly Ser Ser
                            165                 170                 175

Val Gln Trp Ser Asp Pro Leu Pro Glu Cys Arg Glu Ile Tyr Cys Pro
                            180                 185                 190

Ala Pro Pro Gln Ile Asp Asn Gly Ile Ile Gln Gly Glu Arg Asp His
                            195                 200                 205

Tyr Gly Tyr Arg Gln Ser Val Thr Tyr Ala Cys Asn Lys Gly Phe Thr
                            210                 215                 220

Met Ile Gly Glu His Ser Ile Tyr Cys Thr Val Asn Asn Asp Glu Gly
            225                 230                 235                 240

Glu Trp Ser Gly Pro Pro Glu Cys Arg Gly Gly Gly Gly
                            245                 250                 255

Gly Gly Gly Gly Gly Gly Gly Gly Lys Cys Gly Pro Pro Pro
                            260                 265                 270

Ile Asp Asn Gly Asp Ile Thr Ser Phe Pro Leu Ser Val Tyr Ala Pro
                            275                 280                 285

Ala Ser Ser Val Glu Tyr Gln Cys Gln Asn Leu Tyr Gln Leu Glu Gly
                            290                 295                 300

Asn Lys Arg Ile Thr Cys Arg Asn Gly Gln Trp Ser Glu Pro Pro Lys
            305                 310                 315                 320

Cys Leu His Pro Cys Val Ile Ser Arg Glu Ile Met Glu Asn Tyr Asn
                            325                 330                 335

Ile Ala Leu Arg Trp Thr Ala Lys Gln Lys Leu Tyr Ser Arg Thr Gly
                            340                 345                 350

Glu Ser Val Glu Phe Val Cys Lys Arg Gly Tyr Arg Leu Ser Ser Arg
                            355                 360                 365

Ser His Thr Leu Arg Thr Thr Cys Trp Asp Gly Lys Leu Glu Tyr Pro
                            370                 375                 380

Thr Cys Ala
            385

<210> SEQ ID NO 12
            <211> LENGTH: 379
            <212> TYPE: PRT
            <213> ORGANISM: Artificial
```

<220> FEATURE:
<223> OTHER INFORMATION: DAF(1-4)FH(19-20) short linker polypeptide

<400> SEQUENCE: 12

```
Asp Cys Gly Leu Pro Pro Asp Val Pro Asn Ala Gln Pro Ala Leu Glu
1               5                   10                  15
Gly Arg Thr Ser Phe Pro Glu Asp Thr Val Ile Thr Tyr Lys Cys Glu
            20                  25                  30
Glu Ser Phe Val Lys Ile Pro Gly Glu Lys Asp Ser Val Ile Cys Leu
        35                  40                  45
Lys Gly Ser Gln Trp Ser Asp Ile Glu Glu Phe Cys Asn Arg Ser Cys
    50                  55                  60
Glu Val Pro Thr Arg Leu Asn Ser Ala Ser Leu Lys Gln Pro Tyr Ile
65                  70                  75                  80
Thr Gln Asn Tyr Phe Pro Val Gly Thr Val Val Glu Tyr Glu Cys Arg
                85                  90                  95
Pro Gly Tyr Arg Arg Glu Pro Ser Leu Ser Pro Lys Leu Thr Cys Leu
            100                 105                 110
Gln Asn Leu Lys Trp Ser Thr Ala Val Glu Phe Cys Lys Lys Lys Ser
        115                 120                 125
Cys Pro Asn Pro Gly Glu Ile Arg Asn Gly Gln Ile Asp Val Pro Gly
    130                 135                 140
Gly Ile Leu Phe Gly Ala Thr Ile Ser Phe Ser Cys Asn Thr Gly Tyr
145                 150                 155                 160
Lys Leu Phe Gly Ser Thr Ser Ser Phe Cys Leu Ile Ser Gly Ser Ser
                165                 170                 175
Val Gln Trp Ser Asp Pro Leu Pro Glu Cys Arg Glu Ile Tyr Cys Pro
            180                 185                 190
Ala Pro Pro Gln Ile Asp Asn Gly Ile Ile Gln Gly Glu Arg Asp His
        195                 200                 205
Tyr Gly Tyr Arg Gln Ser Val Thr Tyr Ala Cys Asn Lys Gly Phe Thr
    210                 215                 220
Met Ile Gly Glu His Ser Ile Tyr Cys Thr Val Asn Asn Asp Glu Gly
225                 230                 235                 240
Glu Trp Ser Gly Pro Pro Glu Cys Arg Gly Pro Gly Gly Lys
                245                 250                 255
Cys Gly Pro Pro Pro Ile Asp Asn Gly Asp Ile Thr Ser Phe Pro
            260                 265                 270
Leu Ser Val Tyr Ala Pro Ala Ser Ser Val Glu Tyr Gln Cys Gln Asn
        275                 280                 285
Leu Tyr Gln Leu Glu Gly Asn Lys Arg Ile Thr Cys Arg Asn Gly Gln
    290                 295                 300
Trp Ser Glu Pro Pro Lys Cys Leu His Pro Cys Val Ile Ser Arg Glu
305                 310                 315                 320
Ile Met Glu Asn Tyr Asn Ile Ala Leu Arg Trp Thr Ala Lys Gln Lys
                325                 330                 335
Leu Tyr Ser Arg Thr Gly Glu Ser Val Glu Phe Val Cys Lys Arg Gly
            340                 345                 350
Tyr Arg Leu Ser Ser Arg Ser His Thr Leu Arg Thr Thr Cys Trp Asp
        355                 360                 365
Gly Lys Leu Glu Tyr Pro Thr Cys Ala Lys Arg
    370                 375
```

<210> SEQ ID NO 13

<211> LENGTH: 1781
<212> TYPE: DNA
<213> ORGANISM: Artificial
<220> FEATURE:
<223> OTHER INFORMATION: DAF 1-4_FH19-20_CR1_15-17 encoding Pichia
      optimized

<400> SEQUENCE: 13

| | | | | | |
|---|---|---|---|---|---|
| ctgcaggaga | ttgcggttta | ccaccagatg | ttccaaacgc | tcaaccagct | ttggagggta | 60 |
| gaacttcatt | cccagaggac | accgttatca | cctacaagtg | tgaagagtcc | ttcgtcaaga | 120 |
| tcccaggtga | aaaggactcc | gtcatctgtt | tgaagggttc | tcagtggtcc | gacatcgaag | 180 |
| agttctgtca | agatcctgt | gaggtcccaa | ccagattgaa | ctctgcttcc | ttgaagcagc | 240 |
| cttacatcac | ccagaactac | ttcccagttg | gtactgttgt | tgagtacgag | tgcagaccag | 300 |
| gttacagaag | agaaccatct | ttgtccccaa | agctgacctg | cttgcaaaac | ttgaagtggt | 360 |
| ccactgccgt | tgagttctgc | aagaagaagt | cttgtccaaa | cccaggtgag | atcagaaacg | 420 |
| gtcagattga | tgttccaggt | ggtatcttgt | tcggtgctac | tatctccttc | tcctgcaaca | 480 |
| ccggttacaa | gttgttcggt | tctacctcct | ccttctgctt | gatttctggt | tcctctgttc | 540 |
| aatggtccga | cccattgcca | gaatgcagag | aaatctactg | tccagctcca | ccacagatcg | 600 |
| acaacggtat | tattcagggt | gagagagatc | actacggtta | cagacagtcc | gttacctacg | 660 |
| cttgcaacaa | gggtttcact | atgattggtg | agcactccat | ctactgcacc | gttaacaacg | 720 |
| atgaaggtga | atggtctggt | ccaccaccag | aatgtagagg | tggtggagga | ggaggcggtg | 780 |
| gaggtggagg | tggtggtgga | ggaaaatgtg | gaccaccacc | accaattgac | aacggtgaca | 840 |
| ttacttcctt | cccattgtcc | gtttacgctc | cagcttcttc | cgttgagtac | cagtgtcaaa | 900 |
| acctgtacca | gttggagggt | aacaagagaa | tcacctgtag | aaacggtcaa | tggtctgagc | 960 |
| caccaaagtg | cttgcaccca | tgtgttatct | ccagagaaat | catggaaaac | tacaacattg | 1020 |
| ccctgagatg | gaccgccaag | caaaagttgt | actccagaac | tggtgagtcc | gttgagttcg | 1080 |
| tctgtaagag | aggttacaga | ctgtcctcca | gatcccacac | tttgagaact | acttgttggg | 1140 |
| acggaaagtt | ggagtaccct | acttgtgccg | gaggtggagg | aggaggagga | cattgtcaag | 1200 |
| ctccagatca | cttcttgttc | gccaagctta | agactcagac | tcaggcttcc | gatttcccaa | 1260 |
| tcggtacttc | cttgaagtac | gaatgtagac | cagagtacta | cggtagaccc | ttctccatca | 1320 |
| cttgcttgga | caacttggtt | tggtcctctc | caaaggacgt | ctgcaagaga | agtcctgta | 1380 |
| agactccacc | agacccagtt | aacggtatgg | ttcacgttat | caccgacatc | caggttggtt | 1440 |
| ccagaatcca | gtactcctgt | actaccggtc | acagattgat | tggtcactct | tccgctgagt | 1500 |
| gtatcttgtc | cggtaacact | gctcactggt | ctactaagcc | accaatctgt | cagagaatcc | 1560 |
| catgtggttt | gccaccaact | attgctaacg | gtgacttcat | ctccaccaac | agagagaact | 1620 |
| tccactacgg | ttccgttgtc | acctacagat | gtaacttggg | ttccagaggt | agaaaggtgt | 1680 |
| tcgagttggt | tggtgaacca | tccatctact | gtacttccaa | cgacgaccag | gttggtatttt | 1740 |
| ggtctggtcc | tgctccacag | tgcatcatct | aatagtctag | a | | 1781 |

<210> SEQ ID NO 14
<211> LENGTH: 1607
<212> TYPE: DNA
<213> ORGANISM: Artificial
<220> FEATURE:
<223> OTHER INFORMATION: CR1-1-3_FH19-20_CR1-15-17 encoding Pichia
      optimized

<400> SEQUENCE: 14

```
ctgcaggaca atgtaacgct ccagaatggt tgccattcgc tagaccaact caattgactg    60
acgagttcga gttcccaatc ggaacatact tgaactacga gtgcagacca ggttactccg   120
gtagaccatt ctccatcatc tgcttgaaga actccgtttg gactggtgcc aaggacagat   180
gtagaagaaa gtcctgtaga aacccaccag acccagttaa cggtatggtt cacgttatca   240
agggtatcca gttcggttcc cagatcaagt actcctgtac caagggttac agactgattg   300
gttcttcctc cgccacttgt attatctccg gtgacactgt tatctgggac aagagactc    360 caatctgcga cagaattcca tgtggtttgc caccaactat caccaacggt gacttcatct   420
ccaccaacag agaaacttc  cactacggtt ccgttgtcac ctacagatgt aacccaggtt   480
ctggtggtag aaaggttttc gagttggttg gtgagccatc catctactgt acttccaacg   540
atgaccaggt tggtatttgg tctggtccag ctccacagtg tattattggt ggtggaggag   600
gtggtggagg tggaggcggt ggtggtggaa atgtggtcc acctcctcct attgacaacg    660
gtgacattac ttccttccca ttgtccgttt acgctccagc ttcttccgtt gagtaccagt   720
gtcaaaacct gtaccagttg gagggtaaca agagaatcac ctgtagaaac ggtcaatggt   780
ccgaaccacc aaagtgcttg cacccatgtg ttatctccag agaaatcatg gaaaactaca   840
acattgccct gagatggacc gccaagcaaa agttgtactc cagaactggt gagtccgttg   900
agttcgtctg taagagagt  tacagattgt cctccagatc ccacactttg agaactactt   960
gttgggacgg aaagttggag taccctactt gtgccggagg tggaggagga ggaggacatt  1020
gtcaagctcc agatcacttc ttgttcgcca agcttaagac tcagactcag gcttccgatt  1080
tccctattgg tacttccctg aagtacgaat gtagacctga gtactatggt agacccttct  1140
ctatcacctg tctggacaac ttggtttggt cctctccaaa ggacgtctgc aagagaaagt  1200
cttgtaagac tccacctgac cccgtcaatg gaatggtcca tgttattacc gacatccagg  1260
tcggatccag aattcagtac tcttgtacta ccggtcacag actgatcggt cactcttctg  1320
ctgagtgtat cttgtccggt aacactgctc actggtctac taagccacca atctgtcaga  1380
gaatcccttg tggattgcca cctaccattg ctaacggtga tttcattagt accaacaggg  1440 aaaatttca ttacggatct gtcgtgacct acagatgcaa cttgggttcc agaggtagaa  1500
aagtctttga actggtcgga gaaccttcca tctactgcac atctaacgac gatcaagtcg  1560
gaatctggtc tggacctgca cctcaatgta tcatctagta atctaga                1607
```

<210> SEQ ID NO 15
<211> LENGTH: 1465
<212> TYPE: DNA
<213> ORGANISM: Artificial
<220> FEATURE:
<223> OTHER INFORMATION: DAF 1-4_FH19-20_short-linker encoding Pichia
    optimized

<400> SEQUENCE: 15

```
aagatgaaac ggcacaaatt ccggctgaag ctgtcatcgg ttactcagat ttagaagggg    60
atttcgatgt tgctgttttg ccattttcca acagcacaaa taacgggtta ttgtttataa   120
atactactat tgccagcatt gctgctaaag aagaagggt atctctcgag aaagagagg    180 ctgaagctgc aggtgattgt ggtttgccac cagatgttcc aaacgctcaa ccagctttgg   240
agggtagaac tcattcccca gaggacactg ttatcactta caagtgtgaa gagtccttcg   300
ttaagatccc aggtgagaag gactccgtta tctgtttgaa gggttctcag tggtccgaca   360
tcgaagagtt ctgtaacaga tcctgtgagg ttccaactag attgaactcc gcttccttga   420
```

| | |
|---|---|
| agcagcctta catcactcag aactacttcc cagttggtac tgttgttgag tacgagtgta | 480 |
| gaccaggtta cagaagagaa ccatccttgt ccccaaagtt gacttgtttg cagaacttga | 540 |
| agtggtccac tgctgttgag ttctgtaaga agaagtcctg tccaaaccca ggtgagatca | 600 |
| gaaacggtca gattgatgtt ccaggtggta tcttgttcgg tgctactatc tccttctcct | 660 |
| gtaacactgg ttacaagttg ttcggttcca cttcctcatt ctgtttgatc tccggttcct | 720 |
| ccgttcaatg gtctgatcca ttgccagagt gtagagagat ctactgtcca gctccaccac | 780 |
| agattgacaa cggtattatt cagggtgaga gagatcacta cggttacaga cagtccgtta | 840 |
| cttacgcttg taacaagggt ttcactatga tcggtgagca ctccatctac tgtactgtta | 900 |
| acaacgacga aggtgagtgg tctggtccac caccagaatg tagaggtccc ggggtggta | 960 |
| aatgtggtcc cccaccacca attgacaacg gtgacattac ttccttccca ttgtccgttt | 1020 |
| acgctccagc ttcttccgtt gagtaccagt gtcagaactt gtaccagttg gagggtaaca | 1080 |
| agagaatcac ttgtagaaac ggtcagtggt ccgagccacc aaaatgtctg cacccatgtg | 1140 |
| ttatctccag agaaatcatg gaaaactaca acattgcttt gagatggact gctaagcaga | 1200 |
| agttgtactc cagaactggt gagtccgttg agttcgtctg taagagaggt tacagattgt | 1260 |
| cctccagatc ccacactttg agaactactt gttgggacgg aaagcttgag tacccaactt | 1320 |
| gtgctaagag ataataatct agaacaaaaa ctcatctcag aagaggatct gaatagcgcc | 1380 |
| gtcgaccatc atcatcatca tcattgagtt tgtagcctta gacatgactg ttcctcagtt | 1440 |
| caagttgggc actacgagaa gcccg | 1465 |

<210> SEQ ID NO 16
<211> LENGTH: 1193
<212> TYPE: DNA
<213> ORGANISM: Artificial
<220> FEATURE:
<223> OTHER INFORMATION: DAF_FH19-20_long-linker encoding Pichia
      optimized

<400> SEQUENCE: 16

| | |
|---|---|
| attatactgc aggagattgc ggtttaccac cagatgttcc aaacgctcaa ccagctttgg | 60 |
| agggtagaac ttcattccca gaggacaccg ttatcaccta caagtgtgaa gagtccttcg | 120 |
| tcaagatccc aggtgaaaag gactccgtca tctgtttgaa gggttctcag tggtccgaca | 180 |
| tcgaagagtt ctgtcaaaga tcctgtgagg tcccaaccag attgaactct gcttccttga | 240 |
| agcagcctta catcacccag aactacttcc cagttggtac tgttgttgag tacgagtgca | 300 |
| gaccaggtta cagaagagaa ccatctttgt ccccaaagct gacctgcttg caaaacttga | 360 |
| agtggtccac tgccgttgag ttctgcaaga agaagtcttg tccaaaccca ggtgagatca | 420 |
| gaaacggtca gattgatgtt ccaggtggta tcttgttcgg tgctactatc tccttctcct | 480 |
| gcaacaccgg ttacaagttg ttcggttcta cctcctcctt ctgcttgatt ctggttcct | 540 |
| ctgttcaatg gtccgaccca ttgccagaat gcagagaaat ctactgtcca gctccaccac | 600 |
| agatcgacaa cggtattatt cagggtgaga gagatcacta cggttacaga cagtccgtta | 660 |
| cctacgcttg caacaagggt ttcactatga ttggtgagca ctccatctac tgcaccgtta | 720 |
| acaacgatga aggtgaatgg tctggtccac caccagaatg tagaggtggt ggaggaggag | 780 |
| gcggtggagg tggaggtggt ggtggaggaa aatgtggacc accaccacca attgacaacg | 840 |
| gtgacattac ttccttccca ttgtccgttt acgctccagc ttcttccgtt gagtaccagt | 900 |
| gtcaaaacct gtaccagttg gagggtaaca agagaatcac ctgtagaaac ggtcaatggt | 960 |

```
ctgagccacc aaagtgcttg cacccatgtg ttatctccag agaaatcatg gaaaactaca    1020
acattgccct gagatggacc gccaagcaaa agttgtactc cagaactggt gagtccgttg    1080
agttcgtctg taagagaggt tacagactgt cctccagatc ccacactttg agaactactt    1140
gttgggacgg aaagttggag taccctactt gtgcctaata gtctagaata tta           1193
```

<210> SEQ ID NO 17
<211> LENGTH: 1404
<212> TYPE: DNA
<213> ORGANISM: Artificial
<220> FEATURE:
<223> OTHER INFORMATION: CR1-1-3_FH19-20_short-linker encoding Pichia
      optimized

<400> SEQUENCE: 17

```
gagagatcaa aaacaacta attattcgaa acgatgagat tccttcaat ttttactgct       60 gttttattcg cagcatcctc cgcattagct gctccagtca acactacaac agaagatgaa    120
acggcacaaa ttccggctga agctgtcatc ggttactcag atttagaagg ggatttcgat    180
gttgctgttt tgccattttc aacagcaca ataacgggt tattgtttat aaatactact     240
attgccagca ttgctgctaa agaagaaggg gtatctctcg agaaaagaga ggctgaagct    300
gcaggacaat gtaacgctcc agagtggttg ccatttgcta gaccaactca gttgactgac    360
gagttcgagt tcccaatcgg tacttacttg aactacgagt gcagacctgg ttattctggt    420
agaccattct ccatcatctg cctgaagaac tctgtttgga ctggtgctaa ggacagatgc    480
agaagaaagt cctgtagaaa cccaccagat ccagttaacg gaatggtcca cgtcattaag    540
ggtattcagt tcggttccca gatcaagtac tcctgtacca agggttacag attgattggt    600
tcctcctccg ctacttgtat tatctccggt gacaccgtta tttgggacca agagactcca    660
atctgcgaca gaattccatg tggattgcca ccaactattg ccaacggtga cttcatctcc    720
actaacagag agaacttcca ctacggttcc gttgttacct acagatgtaa cccaggttct    780
ggtggtagaa aggttttcga gctggttggt gaaccatcca tctactgtac ttccaacgac    840
gaccaagttg gtatttggag tggtccagct ccacaatgca tcatccccgg gggtggtaaa    900
tgtggtcccc caccaccaat tgacaacggt gacattactt ccttcccatt gtccgtttac    960
gctccagctt cttccgttga gtaccagtgt cagaacttgt accagttgga gggtaacaag    1020
agaatcactt gtagaaacgg tcagtggtcc gagccaccaa aatgtctgca cccatgtgtt    1080
atctccagag aaatcatgga aaactacaac attgctttga gatggactgc taagcagaag    1140
ttgtactcca gaactggtga gtccgttgag ttcgtctgta agagaggtta cagattgtcc    1200
tccagatccc acactttgag aactactgt tgggacggaa agcttgagta cccaacttgt    1260
gctaagagat aataatctag aacaaaaact catctcagaa gaggatctga atagcgccgt    1320
cgaccatcat catcatcatc attgagtttg tagccttaga catgactgtt cctcagttca    1380
agttgggcac ttacgagaag accg                                           1404
```

<210> SEQ ID NO 18
<211> LENGTH: 1019
<212> TYPE: DNA
<213> ORGANISM: Artificial
<220> FEATURE:
<223> OTHER INFORMATION: CR1-1-3_FH19-20_long-linker encoding Pichia
      optimized

<400> SEQUENCE: 18

-continued

```
atattactgc aggacaatgt aacgctccag aatggttgcc attcgctaga ccaactcaat      60
tgactgacga gttcgagttc ccaatcggaa catacttgaa ctacgagtgc agaccaggtt     120
actccggtag accattctcc atcatctgct tgaagaactc cgtttggact ggtgccaagg     180
acagatgtag aagaaagtcc tgtagaaacc caccagaccc agttaacggt atggttcacg     240
ttatcaaggg tatccagttc ggttcccaga tcaagtactc ctgtaccaag ggttacagac     300
tgattggttc ttcctccgcc acttgtatta tctccggtga cactgttatc tgggaccaag     360
agactccaat ctgcgacaga attccatgtg gtttgccacc aactatcacc aacggtgact     420
tcatctccac caacagagag aacttccact acggttccgt tgtcacctac agatgtaacc     480
caggttctgg tggtagaaag gttttcgagt tggttggtga gccatccatc tactgtactt     540
ccaacgatga ccaggttggt atttggtctg gtccagctcc acagtgtatt attggtggtg     600
gaggaggtgg tggaggtgga ggcggtggtg gtggaaaatg tggtccacct cctcctattg     660
acaacggtga cattacttcc ttcccattgt ccgtttacgc tccagcttct tccgttgagt     720
accagtgtca aaacctgtac cagttggagg gtaacaagag aatcacctgt agaaacggtc     780
aatggtccga accaccaaag tgcttgcacc catgtgttat ctccagagaa atcatggaaa     840
actacaacat tgccctgaga tggaccgcca agcaaaagtt gtactccaga actggtgagt     900
ccgttgagtt cgtctgtaag agaggttaca gattgtcctc cagatcccac actttgagaa     960
ctacttgttg ggacggaaag ttggagtacc ctacttgtgc ctaatagtct agaatatta     1019
```